United States Patent
Weir et al.

(10) Patent No.: US 10,277,097 B2
(45) Date of Patent: Apr. 30, 2019

(54) MOTOR ASSEMBLY

(71) Applicant: INTUITIVE SURGICAL OPERATIONS, INC., Sunnyvale, CA (US)

(72) Inventors: David W. Weir, Emerald Hills, CA (US); Melody Wu, Sunnyvale, CA (US); Kevin Durant, Alameda, CA (US); Grant Duque, San Jose, CA (US)

( * ) Notice: Subject to any disclaimer, the term of this patent is extended or adjusted under 35 U.S.C. 154(b) by 1100 days.

(21) Appl. No.: 14/154,087

(22) Filed: Jan. 13, 2014

(65) Prior Publication Data

US 2014/0200851 A1 Jul. 17, 2014

Related U.S. Application Data

(60) Provisional application No. 61/752,409, filed on Jan. 14, 2013.

(51) Int. Cl.
| | |
|---|---|
| *H02K 11/00* | (2016.01) |
| *A61B 34/30* | (2016.01) |
| *A61B 18/14* | (2006.01) |
| *A61B 17/00* | (2006.01) |
| *A61B 90/00* | (2016.01) |

(52) U.S. Cl.
CPC .......... *H02K 11/0094* (2013.01); *A61B 34/30* (2016.02); *A61B 18/1445* (2013.01); *A61B 2017/00725* (2013.01); *A61B 2018/1455* (2013.01); *A61B 2090/031* (2016.02); *G05B 2219/2617* (2013.01); *G05B 2219/45117* (2013.01); *G05B 2219/45119* (2013.01)

(58) Field of Classification Search
CPC .................................................. H02K 11/0094
See application file for complete search history.

(56) References Cited

U.S. PATENT DOCUMENTS

| | | |
|---|---|---|
| 6,331,181 B1 | 12/2001 | Tierney et al. |
| 6,866,671 B2 | 3/2005 | Tierney et al. |
| 7,048,745 B2 | 5/2006 | Tierney et al. |

(Continued)

OTHER PUBLICATIONS

Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

*Primary Examiner* — John E Breene
*Assistant Examiner* — Jeffrey C Morgan
(74) *Attorney, Agent, or Firm* — Haynes and Boone, LLP

(57) ABSTRACT

A motor assembly is presented. A motor assembly can include at least one motor; a memory to store calibrated parameters related to the at least one motor; and electronics coupled to the memory, the at least one motor, the electronics including interfaces to couple with a clamping device and a system to control the operation of the at least one motor. The calibrated parameters are determined for the at least one motor with a procedure that includes performing an initial calibration of the at least one motor; wearing in the at least one motor; performing a final calibration of the at least one motor; and storing calibration data in the memory. In some embodiments, the at least one motor can include a clamping motor and/or a firing motor. In some embodiments, lifetime parameters are stored in the memory.

19 Claims, 18 Drawing Sheets

(56) References Cited

U.S. PATENT DOCUMENTS

| | | | |
|---|---|---|---|
| 2006/0108958 A1* | 5/2006 | Brenner | B25J 9/1641 318/432 |
| 2008/0046122 A1 | 2/2008 | Manzo et al. | |
| 2009/0088774 A1* | 4/2009 | Swarup | A61B 34/37 606/130 |
| 2011/0017801 A1* | 1/2011 | Zemlok | A61B 17/07207 227/175.1 |
| 2011/0288573 A1* | 11/2011 | Yates | A61B 17/07207 606/170 |
| 2013/0110130 A1 | 5/2013 | Manzo et al. | |

* cited by examiner

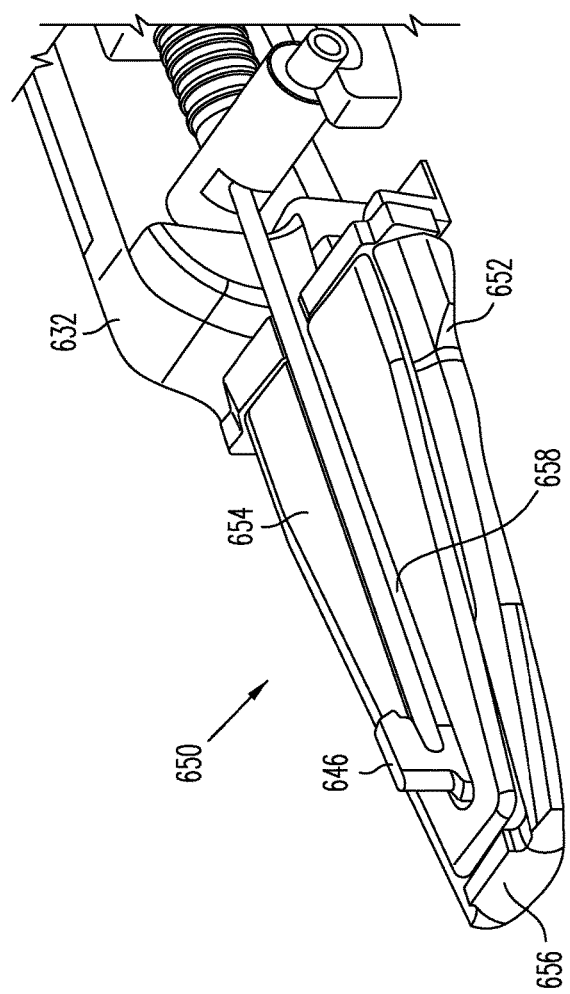
FIG. 6D
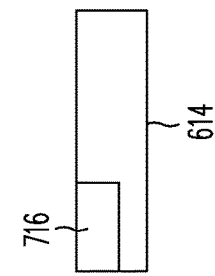
FIG. 7
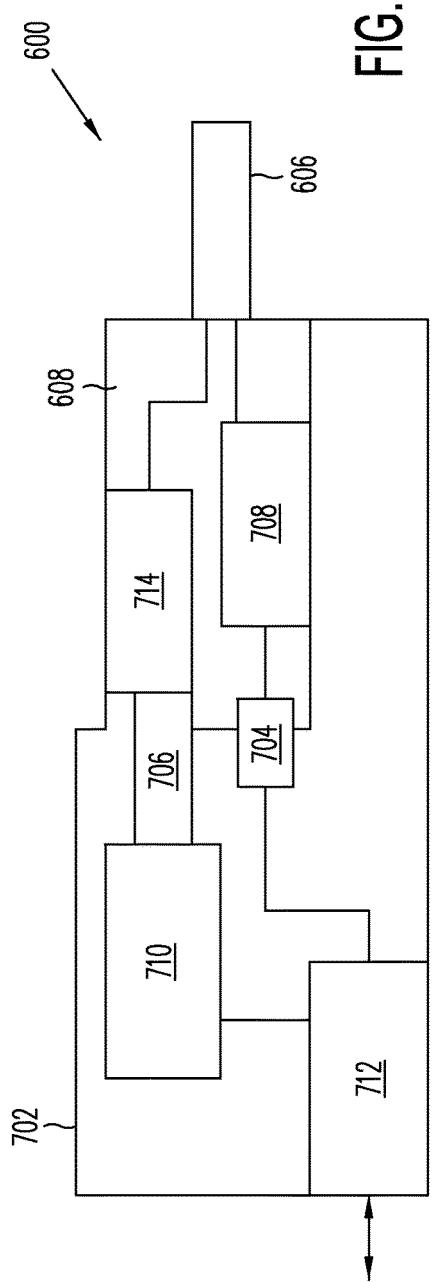

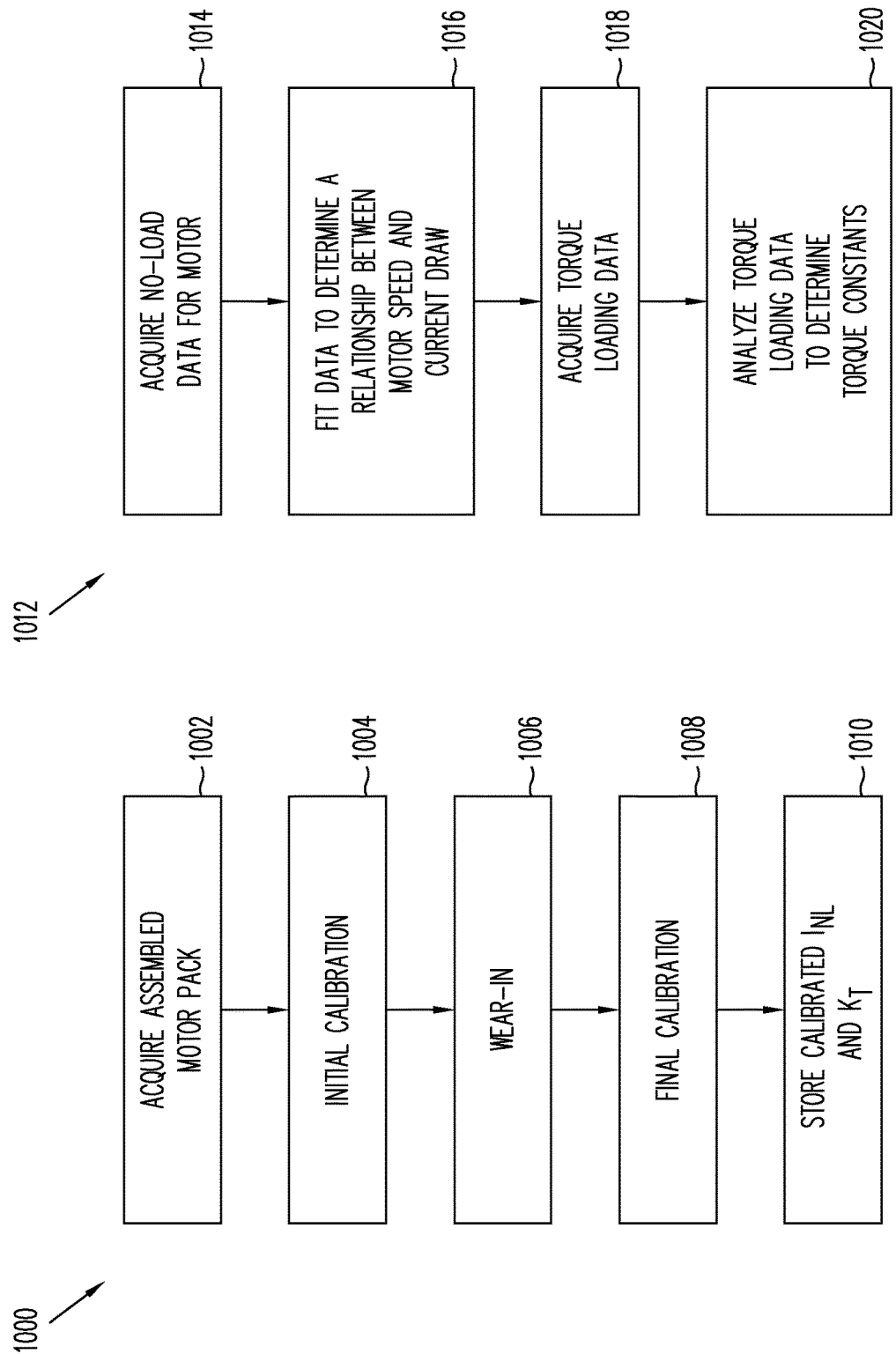

MOTOR ASSEMBLY

CROSS-REFERENCE TO RELATED APPLICATIONS

This application claims priority to provisional application No. 61/752,409, filed Jan. 14, 2013, entitled "Motor Assembly", which is incorporated herein in its entirety by reference.

TECHNICAL FIELD

Embodiments of the present invention are directed to the management of torque parameters in surgical instruments such as staplers or vessel sealers to control the force at the distal tip.

DISCUSSION OF RELATED ART

Minimally invasive surgical techniques are aimed at reducing the amount of extraneous tissue that is damaged during diagnostic or surgical procedures, thereby reducing patient recovery time, discomfort, and deleterious side effects. As a consequence, the average length of a hospital stay for standard surgery may be shortened significantly using minimally invasive surgical techniques. Also, patient recovery times, patient discomfort, surgical side effects, and time away from work may also be reduced with minimally invasive surgery.

A common form of minimally invasive surgery is endoscopy, and a common form of endoscopy is laparoscopy, which is minimally invasive inspection and surgery inside the abdominal cavity. In standard laparoscopic surgery, a patient's abdomen is insufflated with gas, and cannula sleeves are passed through small (approximately one-half inch or less) incisions to provide entry ports for laparoscopic instruments.

Laparoscopic surgical instruments generally include an endoscope (e.g., laparoscope) for viewing the surgical field and tools for working at the surgical site. The working tools are typically similar to those used in conventional (open) surgery, except that the working end or end effector of each tool is separated from its handle by an extension tube (also known as, e.g., an instrument shaft or a main shaft). The end effector can include, for example, a clamp, grasper, scissor, stapler, vessel sealer, cautery tool, linear cutter, needle holder, or other instrument.

To perform surgical procedures, the surgeon passes working tools through cannula sleeves to an internal surgical site and manipulates them from outside the abdomen. The surgeon views the procedure from a monitor that displays an image of the surgical site taken from the endoscope. Similar endoscopic techniques are employed in, for example, arthroscopy, retroperitoneoscopy, pelviscopy, nephroscopy, cystoscopy, cisternoscopy, sinoscopy, hysteroscopy, urethroscopy, and the like.

Minimally invasive telesurgical robotic systems are being developed to increase a surgeon's dexterity when working on an internal surgical site, as well as to allow a surgeon to operate on a patient from a remote location (outside the sterile field). In a telesurgery system, the surgeon is often provided with an image of the surgical site at a control console. While viewing a three dimensional image of the surgical site on a suitable viewer or display, the surgeon performs the surgical procedures on the patient by manipulating master input or control devices of the control console. Each of the master input devices controls the motion of a servo-mechanically actuated/articulated surgical instrument. During the surgical procedure, the telesurgical system can provide mechanical actuation and control of a variety of surgical instruments or tools having end effectors that perform various functions for the surgeon, for example, holding or driving a needle, grasping a blood vessel, dissecting tissue, or the like, in response to manipulation of the master input devices.

Manipulation and control of these end effectors is a particularly beneficial aspect of robotic surgical systems. For this reason, it is desirable to provide surgical tools that include mechanisms that provide three degrees of rotational movement of an end effector to mimic the natural action of a surgeon's wrist. Such mechanisms should be appropriately sized for use in a minimally invasive procedure and relatively simple in design to reduce possible points of failure. In addition, such mechanisms should provide an adequate range of motion to allow the end effector to be manipulated in a wide variety of positions.

Surgical clamping and cutting instruments (e.g., non-robotic linear clamping, stapling, and cutting devices, also known as surgical staplers; and electrosurgical vessel sealing devices) have been employed in many different surgical procedures. For example, a surgical stapler can be used to resect a cancerous or anomalous tissue from a gastro-intestinal tract. Many known surgical clamping and cutting instruments, including known surgical staplers, have opposing jaws that clamp tissue and an articulated knife to cut the clamped tissue between the inserted staples.

The operation of a surgical stapler typically involves the transfer of a relatively high amount of force to the end effector of the surgical stapler. One way of transferring force involves transferring rotary motion from actuators to the end effector. Under-clamping by providing too little force to the end effector can result in less than a complete clamp, leaving a large tissue gap and resulting in inadequately formed staples. Over-clamping by providing too much force to the end effectors can result in increased deflection of the end effector and again result in a large tissue gap, which may result in inadequately formed staples.

Similar considerations can be applied to vessel sealers. A vessel sealer clamps the tissue, seals two sides, and divides the tissue between the seals with a knife. Again, improper clamping can result in improper sealing of the tissue.

Therefore, there is a need to control the clamping of an instrument to provide for proper clamping during operation.

SUMMARY

In accordance with some embodiments of the present invention a calibrated motor assembly is provided. A method of calibrating a motor in a motor assembly according to the present invention includes acquiring an assembled motor assembly; performing an initial calibration of the motor in the motor assembly; wearing in the motor; performing a final calibration of the motor; and storing calibration data in the motor assembly.

A motor assembly according to some embodiments of the invention can include at least one motor; a memory to store calibrated parameters related to the at least one motor; and electronics coupled to the memory, the at least one motor, the electronics including interfaces to couple with a clamping device and a system to control the operation of the at least one motor. The calibrated parameters are determined for the at least one motor with a procedure that includes performing an initial calibration of the at least one motor; wearing in the at least one motor; performing a final calibration of the at least one motor; and storing calibration data in the memory. In some embodiments, the at least one motor includes a clamping motor. In some embodiments, the at least one motor includes a firing motor. In some embodiments, lifetime parameters are stored in the memory.

These and other embodiments are further discussed below with respect to the following figures.

BRIEF DESCRIPTION OF THE DRAWINGS

FIGS. 6C and 6D illustrate a vessel sealer.

FIG. 7 illustrates coupling of a surgical stapler as illustrated in FIGS. 6A and 6B with a motor assembly.

FIGS. 10A and 10B illustrate a procedure for calibrating a motor assembly according to some embodiments of the present invention.

Figure 1:
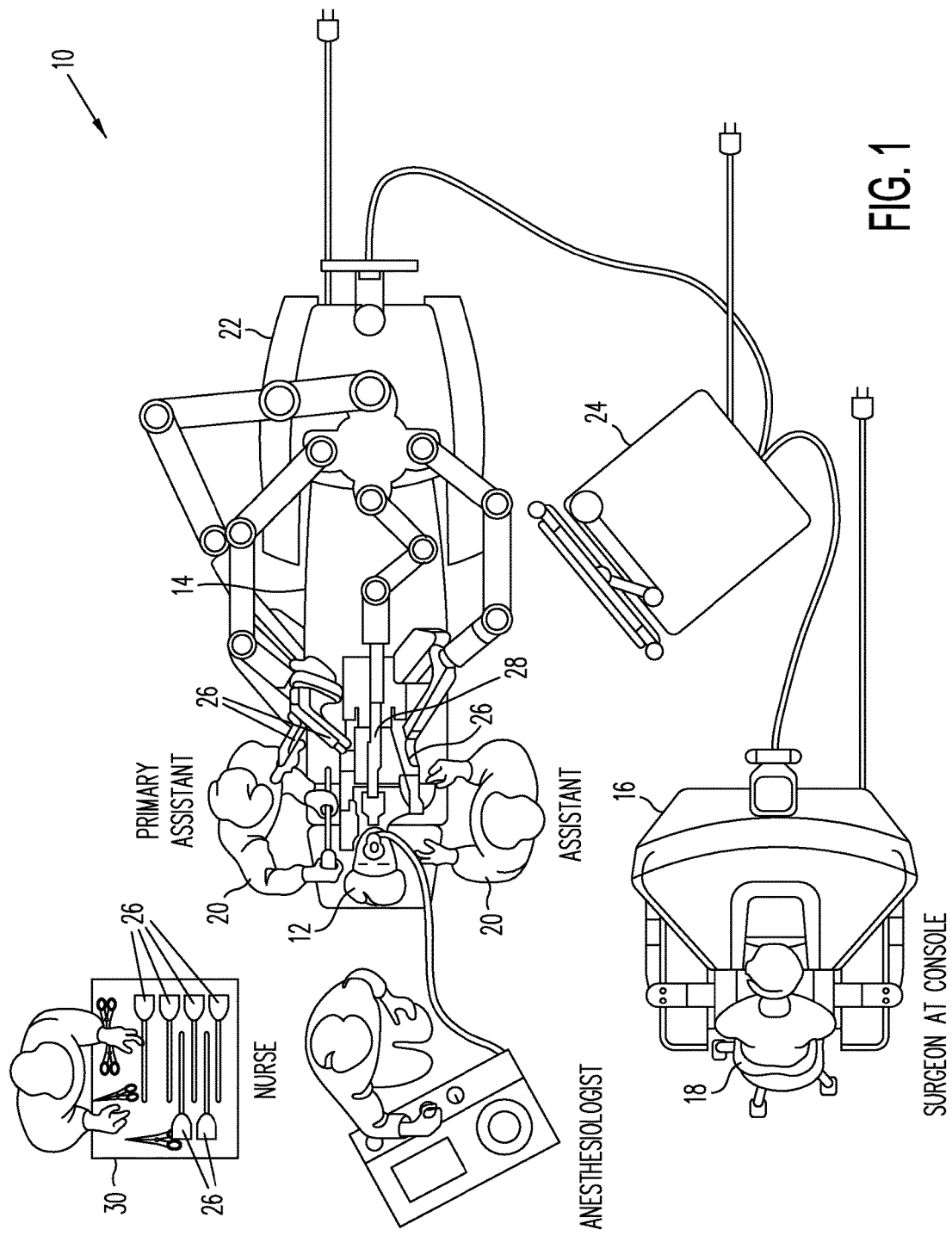
FIG. 1 is a plan view of a minimally invasive robotic surgery system being used to perform a procedure.

In the figures, elements provided with the same element number have the same or similar function.

DETAILED DESCRIPTION

In the following description, specific details are set forth describing some embodiments of the present invention. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure.

This description and the accompanying drawings that illustrate inventive aspects and embodiments should not be taken as limiting—the claims define the protected invention. Various mechanical, compositional, structural, and operational changes may be made without departing from the spirit and scope of this description and the claims. In some instances, well-known structures and techniques have not been shown or described in detail in order not to obscure the invention.

Additionally, the drawings are not to scale. Relative sizes of components are for illustrative purposes only and do not reflect the actual sizes that may occur in any actual embodiment of the invention. Like numbers in two or more figures represent the same or similar elements.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly. Likewise, descriptions of movement along and around various axes includes various special device positions and orientations. In addition, the singular forms "a", "an", and "the" are intended to include the plural forms as well, unless the context indicates otherwise. And, the terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

Elements and their associated aspects that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

Minimally Invasive Robotic Surgery

FIG. 1 shows a plan view illustration of a Minimally Invasive Robotic Surgical (MIRS) system 10, typically used for performing a minimally invasive diagnostic or surgical procedure on a Patient 12 who is lying on an Operating table 14. The system can include a Surgeon's Console 16 for use by a Surgeon 18 during the procedure. One or more Assistants 20 may also participate in the procedure. The MIRS system 10 can further include a Patient Side Cart 22 (surgical robot) and an Electronics Cart 24. The Patient Side Cart 22 can manipulate at least one removably coupled tool assembly 26 (hereinafter simply referred to as a "tool") through a minimally invasive incision in the body of the Patient 12 while the Surgeon 18 views the surgical site through the Console 16. An image of the surgical site can be obtained by an endoscope 28, such as a stereoscopic endoscope, which can be manipulated by the Patient Side Cart 22 to orient the endoscope 28. The Electronics Cart 24 can be used to process the images of the surgical site for subsequent display to the Surgeon 18 through the Surgeon's Console 16. The number of surgical tools 26 used at one time will generally depend on the diagnostic or surgical procedure and the space constraints within the operating room among other factors. If it is necessary to change one or more of the tools 26 being used during a procedure, an Assistant 20 may remove the tool 26 from the Patient Side Cart 22, and replace it with another tool 26 from a tray 30 in the operating room.

Figure 2:
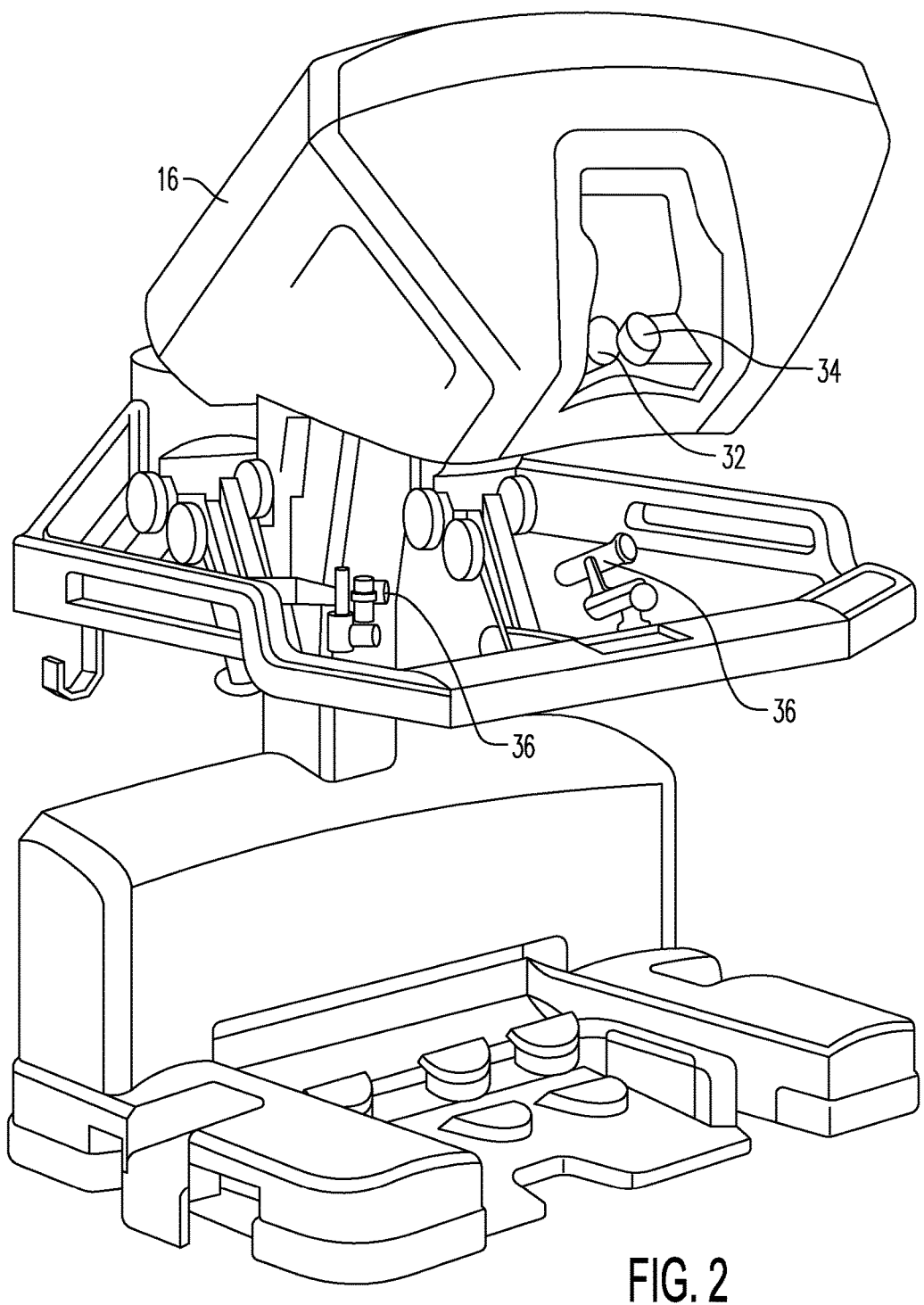
FIG. 2 is a perspective view of a surgeon's control console for a robotic surgery system shown in FIG. 1.

FIG. 2 is a perspective view of the Surgeon's Console 16. The Surgeon's Console 16 includes a left eye display 32 and a right eye display 34 for presenting the Surgeon 18 with a coordinated stereo view of the surgical site that enables depth perception. The Console 16 further includes one or more input control devices 36, which in turn cause the Patient Side Cart 22 (shown in FIG. 1) to manipulate one or more tools. The input control devices 36 can provide the same degrees of freedom as their associated tools 26 (shown in FIG. 1) to provide the Surgeon with telepresence, or the perception that the input control devices 36 are integral with the tools 26 so that the Surgeon has a strong sense of directly controlling the tools 26. To this end, position, force, and tactile feedback sensors (not shown) may be employed to transmit position, force, and tactile sensations from the tools 26 back to the Surgeon's hands through the input control devices 36.

The Surgeon's Console 16 is usually located in the same room as the patient so that the Surgeon may directly monitor the procedure, be physically present if necessary, and speak to an Assistant directly rather than over the telephone or other communication medium. However, the Surgeon can be located in a different room, a completely different building, or other remote location from the Patient allowing for remote surgical procedures.

Figure 3:
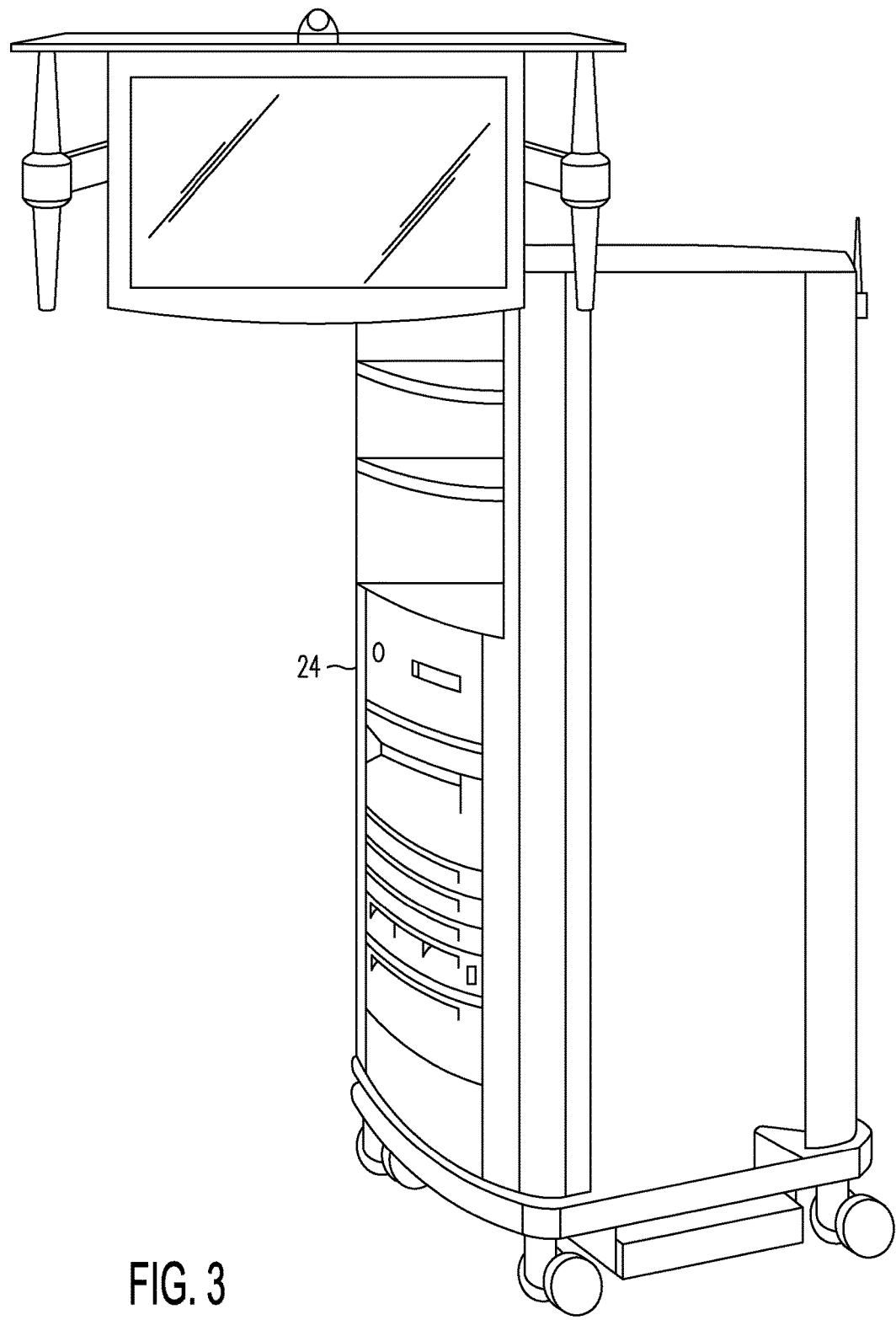
FIG. 3 is a perspective view of a robotic surgery system electronics cart shown in FIG. 1.

FIG. 3 is a perspective view of the Electronics Cart 24. The Electronics Cart 24 can be coupled with the endoscope 28 and can include a processor to process captured images for subsequent display, such as to a Surgeon on the Surgeon's Console, or on another suitable display located locally and/or remotely. For example, where a stereoscopic endoscope is used, the Electronics Cart 24 can process the captured images to present the Surgeon with coordinated stereo images of the surgical site. Such coordination can include alignment between the opposing images and can include adjusting the stereo working distance of the stereoscopic endoscope. As another example, image processing can include the use of previously determined camera calibration parameters to compensate for imaging errors of the image capture device, such as optical aberrations.

Figure 4:
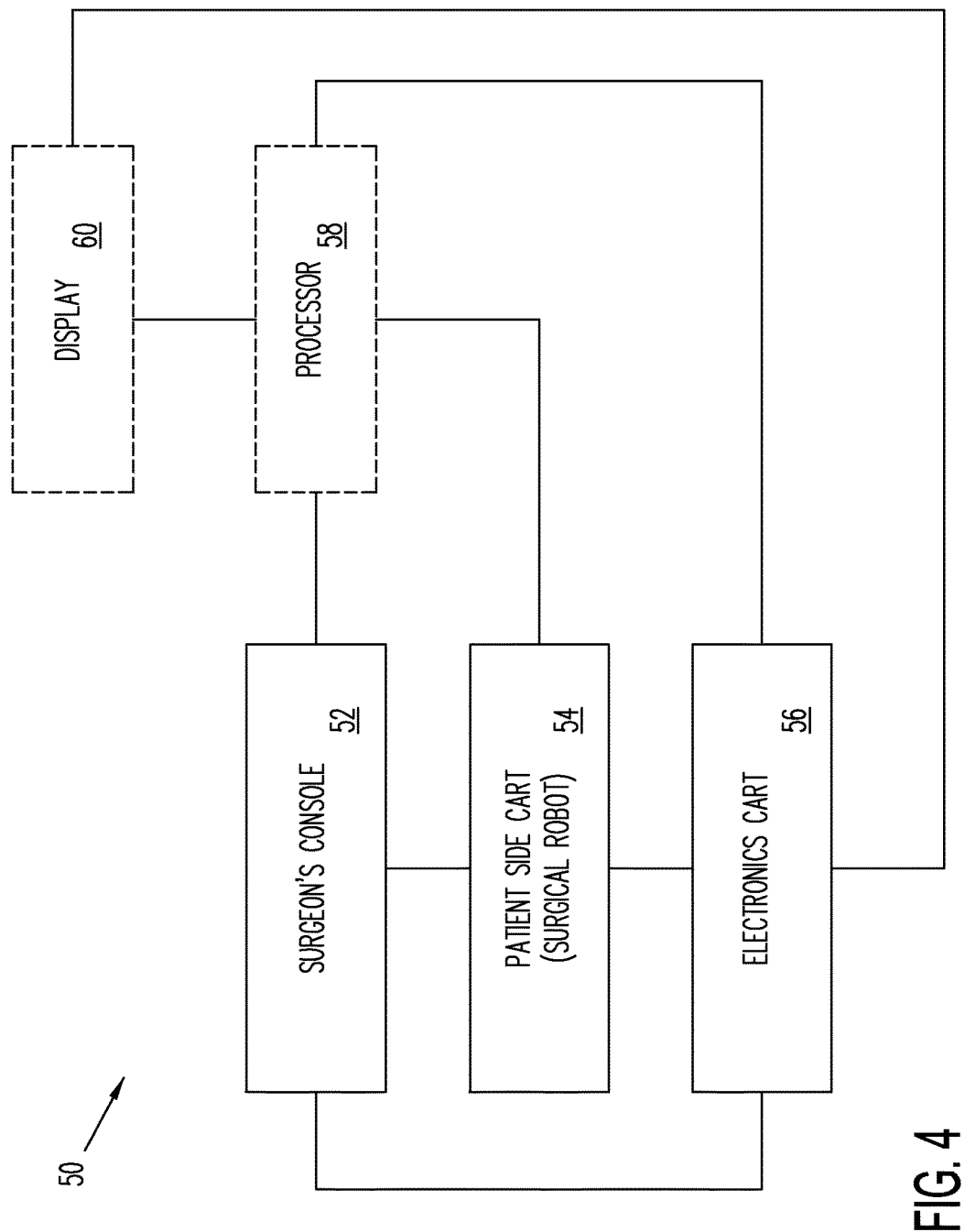
FIG. 4 diagrammatically illustrates a robotic surgery system as shown in FIG. 1.

FIG. 4 diagrammatically illustrates a robotic surgery system 50 (such as MIRS system 10 of FIG. 1). As discussed above, a Surgeon's Console 52 (such as Surgeon's Console 16 in FIG. 1) can be used by a Surgeon to control a Patient Side Cart (Surgical Robot) 54 (such as Patent Side Cart 22 in FIG. 1) during a minimally invasive procedure. The Patient Side Cart 54 can use an imaging device, such as a stereoscopic endoscope, to capture images of the procedure site and output the captured images to an Electronics Cart 56 (such as the Electronics Cart 24 in FIG. 1). As discussed above, the Electronics Cart 56 can process the captured images in a variety of ways prior to any subsequent display. For example, the Electronics Cart 56 can overlay the captured images with a virtual control interface prior to displaying the combined images to the Surgeon via the Surgeon's Console 52. The Patient Side Cart 54 can output the captured images for processing outside the Electronics Cart 56. For example, the Patient Side Cart 54 can output the captured images to a processor 58, which can be used to process the captured images. The images can also be processed by a combination of the Electronics Cart 56 and the processor 58, which can be coupled together to process the captured images jointly, sequentially, and/or combinations thereof. One or more separate displays 60 can also be coupled with the processor 58 and/or the Electronics Cart 56 for local and/or remote display of images, such as images of the procedure site, or other related images.

Figure 5:
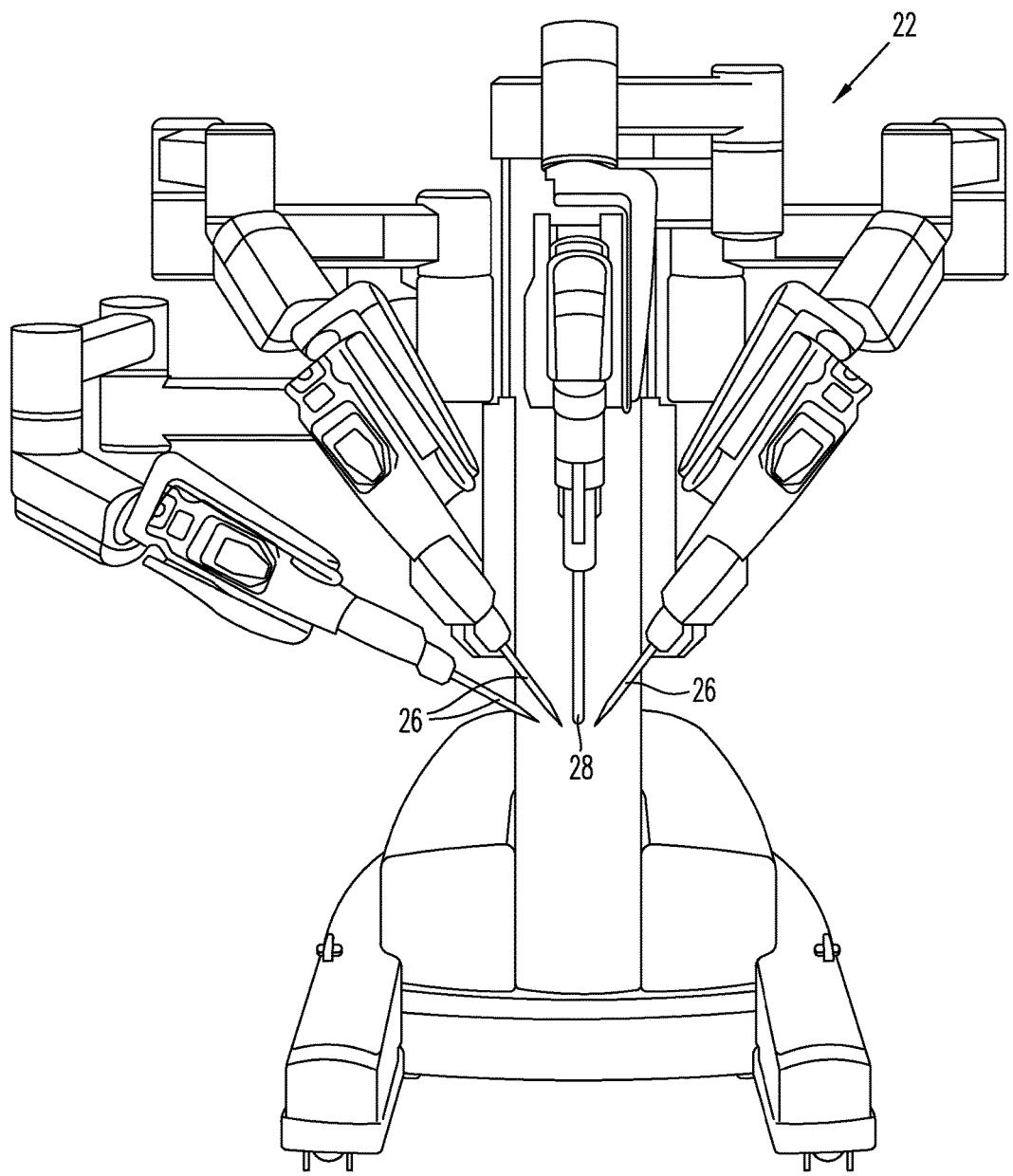
FIG. 5 illustrates a patient side cart of a surgical system as shown in FIG. 1.

FIG. 5 shows a Patient Side Cart 22. The Patient Side Cart 22 shown provides for the manipulation of three surgical tools 26 and an imaging device 28, such as a stereoscopic endoscope used for the capture of images of the site of the procedure. Manipulation is provided by robotic mechanisms having a number of robotic joints. The imaging device 28 and the surgical tools 26 can be positioned and manipulated through incisions in the patient or through an orifice in the patient so that a kinematic remote center is maintained at the incision to minimize the size of the incision. Images of the surgical site can include images of the distal ends of the surgical tools 26 when they are positioned within the field-of-view of the imaging device 28.

FIGS. 1-5 illustrate a multi-port surgical robot. It should be understood that embodiments of the present invention can also be utilized with a single port surgical robot. In either multiport or single port surgeries, surgical tools 26 are passed through cannulas inserted into patient 12 at the surgical site. The surgical tools 26 are manipulated through patient side cart 22 while the surgeon directs and views the procedure from surgeon's console 16. Processor 58 and electronics cart 24 can be utilized to translate inputs from the surgeon at the surgeon's console 16 to actual motion of end effectors of surgical tools 26. Surgical tools that may be typically utilized include clamps, graspers, scissors, staplers, cautery tools, linear cutters, needle holders, and other instruments. Each of the surgical tools 26 is attached to, and driven by, patient side cart 22 under the direction of surgeon 18, as provided by processor 58 and electronics cart 56. Processor 58 and electronics cart 16 translate the inputs from surgeon 18 into driving actions at patient side cart 22 that affect the motions of the end effectors of surgical tools 26. In particular, surgical tools 26 can include one of a stapler or vessel sealer according to the present invention.

Clamping Instrument

Figure 6A:
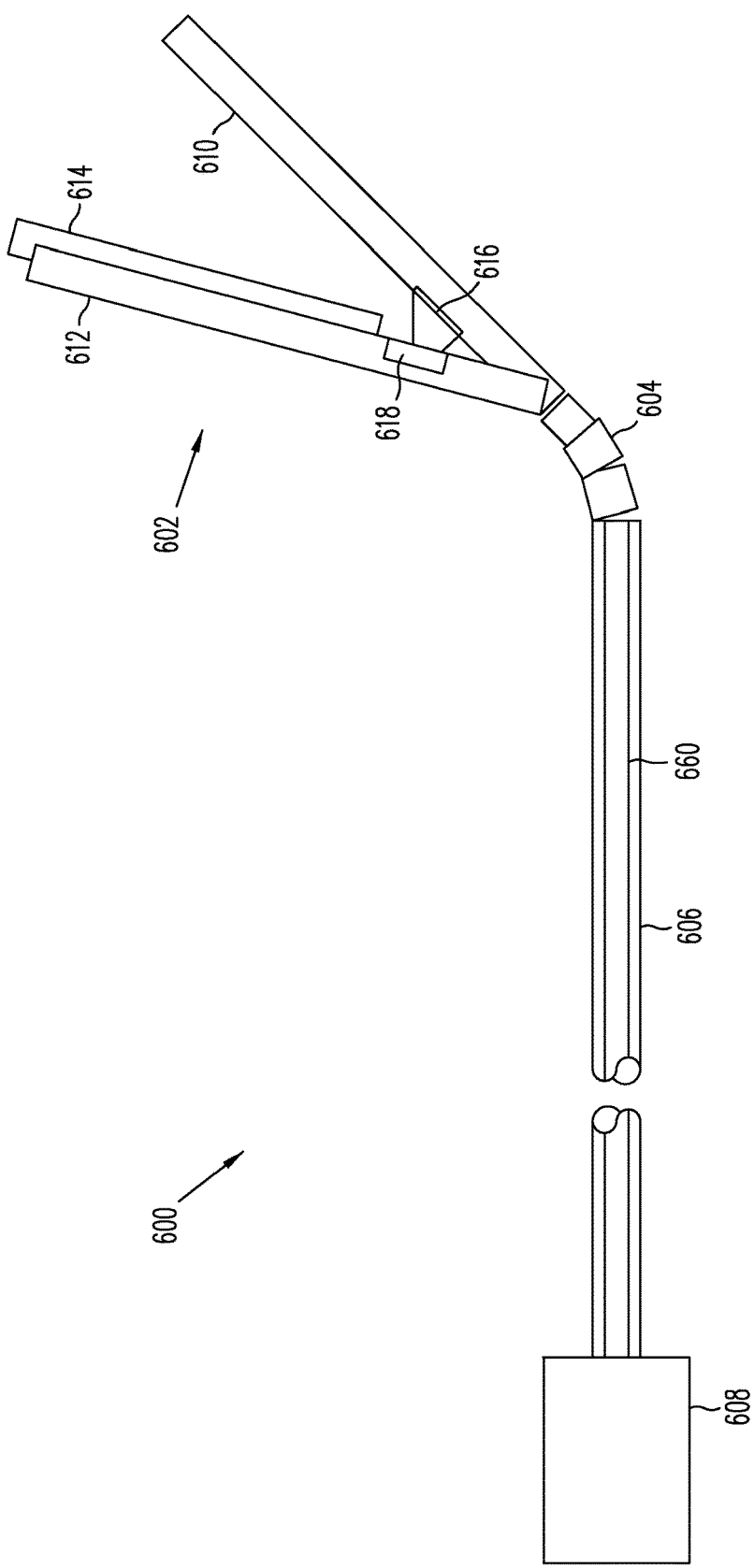
FIGS. 6A and 6B illustrate a surgical stapler.

The surgical tools 26 that can be employed in surgical system 10 can include clamping instruments such as staplers and electronic vessel sealers. Such devices can be used to resect cancerous or anomalous tissue, for example from a gastro-intestinal tract. FIG. 6A illustrates an example of a stapler 600. Stapler 600 includes a stapler end effector 602, a wrist 604, an instrument shaft 606 and a chassis 608.

As shown in FIG. 6A, stapler end effector 602 includes an anvil 610 and a jaw 612. A stapler cartridge 614 can be inserted onto jaw 612. In some embodiments of stapler 600, a cutting knife blade 616 is configured such that it can travel along the long direction of anvil 610. Stapler 600 can be utilized as a grasper, however during operation as a stapler jaw 612 is forced against anvil 610 to clamp tissue between jaw 612 and anvil 610.

A proper tissue gap, the distance between jaw 612 and anvil 610 during clamping, is important for proper staple formation. If the tissue gap is too large, the staples will not properly form during firing. A large tissue gap can be caused by clamping overly thick material between jaw 612 and anvil 610. In some cases, stapler end effector 602 can be driven to a predetermined clamp position and the torque required to achieve this position measured. If the torque is too high, then anvil 610 has deflected and the tissue gap will be too big. In some embodiments, a torque limit can be set and end effector 602 can be moved toward a predetermined clamp position. If the torque limit prevents end effector 602 from achieving the predetermined clamp, then an appropriate tissue gap cannot be achieved. In both cases, accurate sensing or control of the torque acting on anvil 610 is important for accurately detecting inadequate tissue gap When the stapler is fired, staples are forced through the intervening tissue and into anvil 610 by sled 618 traveling along jaw 612. The distance between jaw 612 and anvil 610, which is the tissue gap, determines proper formation of the staples. Controlling the tissue gap can help to ensure proper staple formation. Adequate clamping force between jaw 612 and anvil 610 provides for an appropriate tissue gap for staple formation. Adequate clamping force on the tissue can be a function of cartridge 614, which determines the length of the staples.

Additionally, knife blade 616 (which may be formed as an I-Beam or attached to sled 618) is translated along anvil 610 to separate the stapled tissue. In some embodiments, sled 618 and knife blade 616 are formed within cartridge 614. If the tissue gap is incorrect, the staples may be improperly formed, causing tissue damage and other complications. In some embodiments, stapler 600 may be a linear stapler. Some embodiments may not include knife blade 616 and therefore perform stapling without transection.

Achievement of hemostasis and pneumostasis (the sealing of tissue using a stapling device) depends on providing appropriate pressure, which results from the clamping force, on the tissue after firing such that the staples adequately compress the tissue to prevent bleeding and leaks. Providing too much pressure may result in the staples squeezing the tissue hard enough to cut off the blood supply entirely, preventing the tissue from healing and leading to necrosis.

As discussed above, if too much clamping force is used to position end effector 602 into a predetermined clamp position, then a deflection between the tips of anvil 610 and jaw 612 may result in incorrect clamping. Additionally, too little clamping force and jaw 612 may not fully close against anvil 610 into a predetermined clamp position, again resulting in improper stapling of the tissue.

Stapler cartridge 614 can be color coded for particular circumstance, including tissue thickness. Although several different colors can be utilized, the following chart of color coding may apply:

| Cartridge Color | Tissue Thickness | Open Staple Height (mm) | Closed Staple Height (mm) |
| --- | --- | --- | --- |
| Gray | Mesentery/Thin | 2.0 | 0.75 |
| White | Vascular/Thin | 2.5 | 1.0 |
| Blue | Regular | 3.5 | 1.5 |
| Gold | Regular/Thick | 3.8 | 1.8 |
| Green | Thick | 4.1 | 2.0 |
| Black | Very Thick | 4.4 | 2.3 |

Cartridge 614 may come in various lengths, for example 30, 45, or 60 mm. A single stapler 600 can fire many reloads, with each cartridge being fired once. Cartridge 614 may include data storage that holds, for example, cartridge serial number, cartridge type, part number, style, direction of firing, length of firing, cartridge color, firing torque, maximum deflection and other data. In some embodiments, knife blade 616 and sled 618 are part of cartridge 614 and are replaced with each re-load.

Figure 6B:
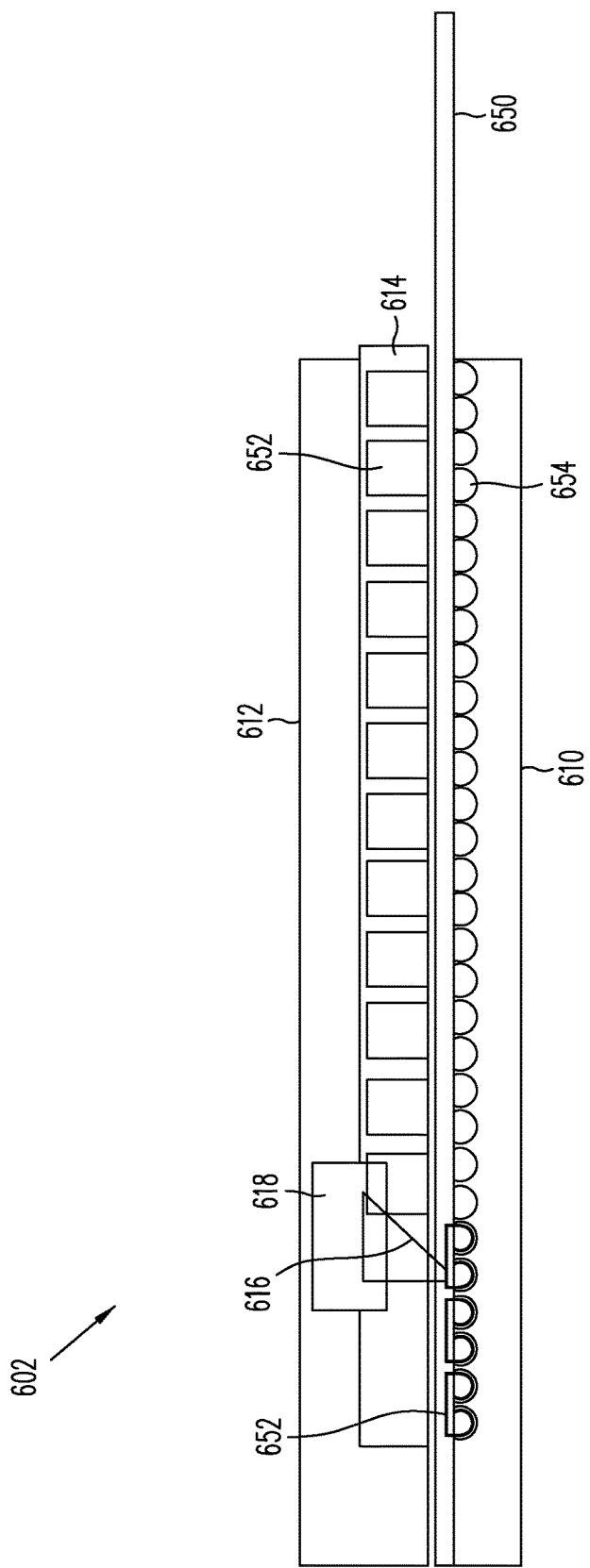

FIG. 6B illustrates staple end effector 602 clamped to tissue 650. As shown in FIG. 6B, cartridge 614 includes staples 652. During firing, sled 618 can travel along jaw 612 to drive staples 652 that are housed in cartridge 614 through the clamped tissue and into pockets 654 on anvil 610. Although FIG. 6B illustrates an embodiment where each leg of staple 652 can be formed into a portion of the "B"-shape by an individual pocket 654, in some embodiments staple 652 can be shaped by a single pocket 654. Pockets 654 are configured to form staples 652 into a "B"-shape, which provides optimal sealing. Knife 616 cuts the tissue between rows of staples to cut the stapled tissue. Cartridge 614 may produce a number of rows of staples, for example two (2) or three (3) rows on each side of the cut formed by knife 616 may be formed.

The clamping action of jaw 612 and anvil 610 and the firing motion of sled 618 and knife 616 are driven by chassis 608 coupling a torque from external motors (not shown in FIG. 6A) to couplers 660. Couplers 660 can be, for example, drive shafts or cables. Couplers 660 travel along shaft 606 and couple to cams, gears, screws, or worm drives in end effector 602 and cartridge 614. Couplers 660 are also utilized to control wrist 604. As shown in FIG. 6A, chassis 608 controls couplers 660 by controlling the tension of cables or rotation of drive shafts that run through instrument shaft 606 to end effector 602. Clamping of jaw 612 against 610 can be managed with a cam mechanism that rotates jaw 612 into anvil 610 or alternatively rotates anvil 610 into jaw 612. The firing of sled 618 and knife 616 can, for example, be driven by a lead screw mechanism driven by a drive shaft coupler 660. In some embodiments, clamping of jaw 612 and anvil 610 and firing of sled 618 and knife 616 can be controlled by rigid drive shafts while control of a normal grip of jaw 612 and anvil 610 as well as the pitch and yaw of wrist 604 can be controlled by cables. In some embodiments, clamping and firing may be controlled by cables.

In order to provide for proper clamping during firing of stapler 600, a particular clamping force is provided between jaw 612 and anvil 610. That clamping force is initially provided by the torque of a motor coupled to chassis 608. The appropriate torque to provide the clamping force may vary from one stapler to another due to manufacturing variances of chassis 608 and friction that may be present for example in shaft 606, wrist 604, and the mechanical operation of jaw 612 and anvil 610. Furthermore, as stapler 600 wears, the appropriate clamping input torque may drift during the lifetime of stapler 600 and it may take less torque applied to chassis 608 to affect the proper clamping force between jaw 612 and anvil 610. Since improper clamping force results in improper tissue gap due to improper deflection of the jaw 612 and anvil 610, if too much torque is applied to chassis 608 or there is improper closing of the jaw 612 and anvil 610 through too little clamping force, then improper formations of staples 652 may occur during firing. Such improper clamping may also damage tissue 650, both as a result of improper staple formation and improper clamping during the process.

As discussed above, a common driving mechanism for clamping jaw 612 against anvil 610 is with utilization of a cam mechanism. Appropriate clamping, however, cannot be determined solely by the position of the cam. This is a result of the flexibility of jaw 612 and anvil 610, which can result in additional separation of the tips of jaw 612 and anvil 610. When too much clamping torque is applied, the tip separation between jaw 612 and anvil 610, the tissue gap, may be too high resulting in improper staple formation during firing. Therefore, in some embodiments of the present invention a torque limit is set and applied to stapler 600 such that excessive tip separation (tissue gap) is prevented during clamping. Firing is only permitted if stapler 600 can reach the fully clamped position while the torque limit is implemented. If the torque limit prevents clamping (stalls), then the tissue cannot be adequately compressed and if clamping were to proceed an excessive tip separation due to the flexibility of the jaw 612 and anvil 610 would result. Stapler 600, therefore, can be considered to be clamped when jaw 612 and anvil 610 have reached full travel (i.e. by achieving the expected number of turns of a leadscrew or cardan) and the torque limit has not been reached.

Figure 6C:
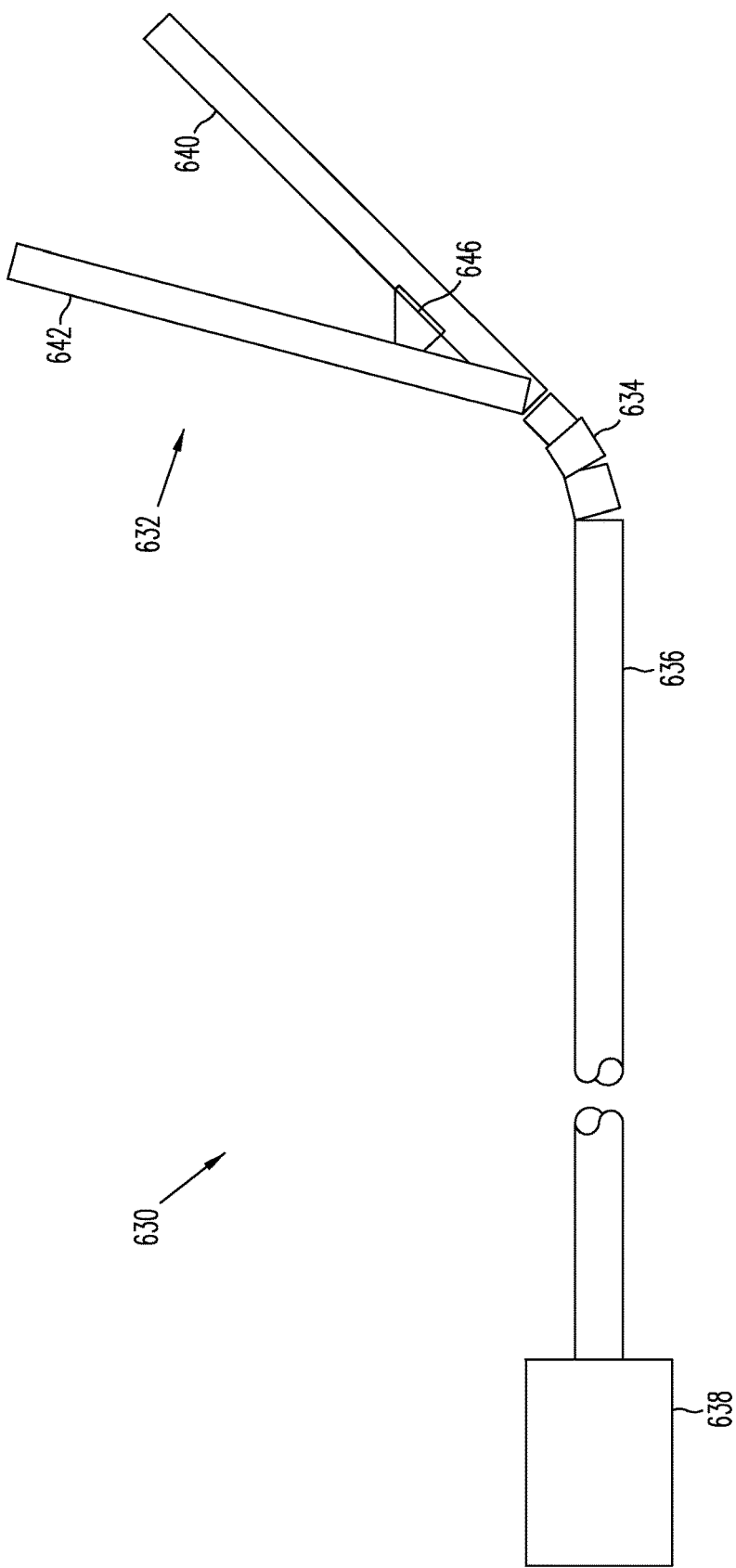

Similar issues occur with a vessel sealer. FIG. 6C illustrates a vessel sealer 630. Vessel sealer 630 includes an end effector 632, wrist 634, an instrument shaft 636 and a chassis 638. End effector 632 includes a jaws 642 and 640, which are clamped onto tissue that is to be sealed. Instead of staples, vessel sealer 630 can utilize an RF method of sealing the tissue clamped between jaws 640 and 642.

FIG. 6D illustrates end effector 632 with jaw 650, which can be either of jaws 640 or 642. As shown in FIG. 6D, jaw 650 includes an electrode 654 embedded in jaw case 652. Knife 646 can be driven along a track 658 formed in electrode 654. Jaw case 652 has tips 656 that extend beyond and above electrode 654 such that a minimum gap between electrodes 654 is maintained during the process. In some embodiments, the minimum gap can be, for example, 0.006 inches. When fired, jaws 640 and 642 can be energized to seal the tissue and knife blade 646 can travel along track 658 in jaws 640 and 642 to divide the tissue. Energy is supplied through electrodes 654 in jaws 640 and anvil 642. In some embodiments, knife blade 646 can be activated separately from the sealing energy.

A proper clamping force is needed to provide for proper seal formation during electrocautery. Excessive clamping force may damage the driving mechanism, for example a leadscrew mechanism. Therefore, operation of vessel sealer 630 depends on providing enough clamping force to jaws 640 and 642 while not damaging vessel sealer 630 itself. The upper force limit is based on the goals of 1) not damaging vessel sealer 630 and 2) providing consistent performance.

This disclosure will focus on operation of stapler 600, although one skilled in the art will recognize that other instruments such as vessel sealer 630 can also benefit. In either stapler 600 or vessel sealer 630, various motions of the end effector are controlled through the chassis by cables running through the instrument shaft. The chassis is driven in order to affect the couplers in the instrument shaft, which in turn control motions at the end effector. As discussed above with respect to stapler 600, the couplers that control clamping and firing can be drive shafts, cables, push-pull rods, or other mechanism. The torque on motors that are utilized to drive the chassis translates to forces applied to various components of the end effector.

FIG. 7 illustrates surgical stapler 600 mounted on a motor assembly 702. Motor assembly 702 can be mounted to the stapler instrument, which is then mounted to the surgical arms of the patient side cart 22. Motor assembly 702 can also be mounted to, or made part of, one of the surgical arms of patient side cart 22. As shown in FIG. 7, motor assembly 702 includes one or more motors 710 that are mechanically coupled through a mechanical coupler 706 and electronics 712. Mechanical coupler 706 can be coupled to chassis 608 when stapler 600 is mounted to motor assembly 702. In some embodiments, the one or more motors 710 may include a clamping motor and a firing motor. The combination of one or more motors 710 and electronics 712 of motor assembly 702 can be referred to as a motor pack. Motors that drive wrist 604 may be included in motor assembly 702 or may be separate from motor assembly 702. Mechanical coupler 706 transmits the torque from the one or more motors 710 into chassis 608, where the torque is transmitted to cables 660 by mechanical converter 714.

Electronics 708 includes storage memory and interface electronics to store and transmit data to motor assembly 702. The data stored in electronics 708 include parameters relevant to surgical stapler 600. Such data can be utilized to identify and control stapler 600 and, for example, may include the serial number, the instrument type, lifetime (i.e. the number of firings), and other information regarding stapler 600. Storing instrument data in electronics 708 has been described, for example, in U.S. Pat. No. 6,866,671, which is herein incorporated by reference in its entirety.

Electronics 708 can also communicate with data storage 716 on cartridge 614 when cartridge 614 is positioned into end effector 602. Data storage 716 can, for example, store data related to the cartridge, including its identification, cartridge lot number, cartridge type, cartridge serial number, cartridge firing status, cartridge color, length, torque offset, and other data. The data stored in data storage 716 of cartridge 614 can be transmitted to a control system for determining how stapler 600, cartridge 614, and motor assembly 702 are to be utilized together.

Motor assembly 702 can include electronics 712 that exchange data through interface 704 with electronics 708, communicates that data and other information through patient side cart 54 to other components of system 10, and receives data and instructions from other components of system 10. Electronics 712 can also store data related to motor assembly 702, for example the motor assembly type, serial number, lifetime (i.e. number of firings lifetime), and other information regarding the operation of motor assembly 702. Electronics 712 may also provide input to the one or more motors 710 that are mechanically coupled to stapler 600 as well as receiving data from sensors monitoring the position of the motors or other components of the mechanism. Such input may be to control and limit the current provided to the one or more motors 710 and may including one or more current loop control circuits and/or position loop control circuits.

Figure 8:
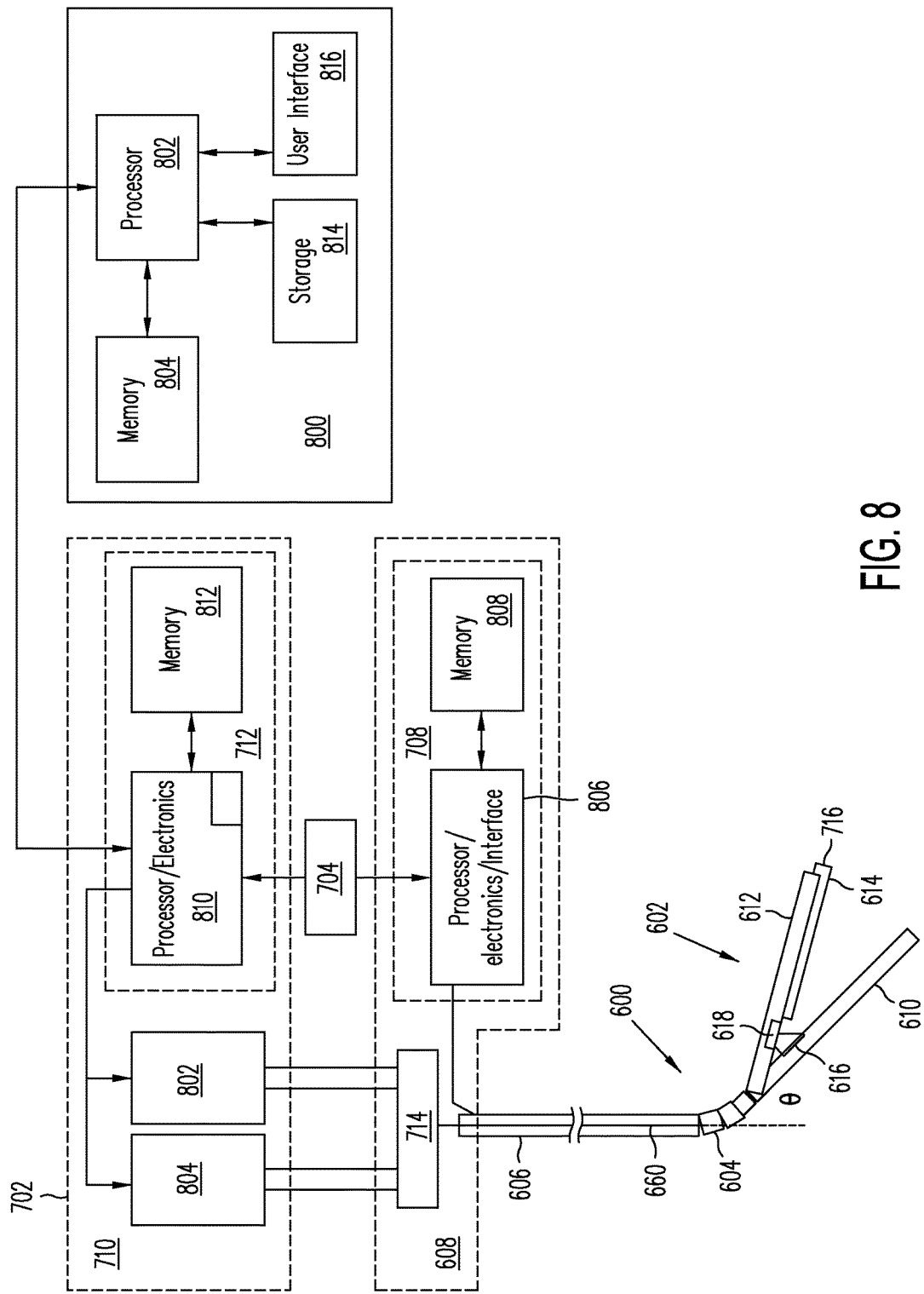
FIG. 8 illustrates operation of a surgical system utilizing a surgical stapler.

FIG. 8 illustrates operation of a surgical system with stapler 600, although another clamping instrument such as a vessel sealer may be utilized. As shown in FIG. 8, electronics 708 of chassis 608 includes a memory 808 and electronics 806. Memory 808 includes non-volatile memory that can store parameters regarding stapler 600. As discussed above, such parameters may include operating parameters of stapler 600, lifetime of stapler 600, type of stapler 600, and other parameters. Electronics 806 is also coupled to read data storage 716 from cartridge 614 and relay those parameters. Electronics 806 can read parameters from memory 808 and parameters from data storage 716 in response to signals received through interface 704.

In some embodiments, interface 704 includes electrical connections between chassis 608 and motor assembly 702. Electronics 806 can include a processor and other electronics that read data from and write data to memory 808.

Electronics 712 of motor assembly 702 includes electronics 810 and memory 812. Electronics 810 can be a processor or other electronics that interfaces to electronics 806 through interface 704. As shown in FIG. 8, electronics 810 also provides control signals to the one or more motors 710. FIG. 8 shows motors 802 and 804. Motors 802 and 804 drive mechanical converter 714 in order that the functions of stapler 602 are performed.

In particular, motor 804 is a clamping motor and operates stapler 600 to provide clamping between jaw 612 and anvil 610 against tissue 650. Motor 802 is a firing motor and operates stapler 600 and cartridge 614 to fire stapler 600. Stapler 600 is fired when the stapler 600 is clamped. A clamped condition can be determined when the output position of motor 804 reaches the appropriate clamp position while simultaneously a torque limit is implemented to prevent excessive tip separation. The torque provided by motor 804 can be controlled by the current provided to motor 804. The current provided to motor 804 can be controlled by electronics 810. In operation, torque limits are provided for motor 804 based upon the instrument and motor assembly (or motor pack) it is used with. Clamping can be determined when the appropriate position of motor 804 is reached while the appropriate torque limit is implemented. The torque limit is directly related to a current limit for motor 804, and therefore the torque limit is reached when the current draw of motor 804 reaches a corresponding current limit.

Electronics 810 may include processors and electronics that execute instructions stored in memory 812. As such, electronics 810 can include current controllers and position controllers for controlling motors 804 and 802, which can be the clamping motor 804 and firing motor 802, respectively. As is further shown in FIG. 8, electronics 810 can include various sensors 820 that monitor the performance of motor assembly 702. Sensors 820 can, for example, include temperature sensors to measure the motor assembly temperature, current sensors to measure the current drawn by each of the at least one motors 710, and position sensors to measure the output position of each of the at least one motors 710.

Memory 812 may include a combination of volatile and non-volatile memory and may store data and executable instructions for controlling the one or more motors 710. Memory 812 can include parameters related to motor assembly 702, including serial number, part number, version number, configuration information (type, style, expiration information, current controller gains, position controller gains, gear ratio), temperature coefficients, wear coefficients, friction coefficients, motor $K_T$ (the parameter that relates torque to current) and other information.

Other functions of stapler 600, for example operation of wrist 604 and translation of sled 618 and knife 616 during firing, can be provided by other motors or combinations of motors operating with mechanical converter 714. As is understood, mechanical converter 714 can be combinations of gears and cams that are coupled to cables 660 to provide the appropriate motions. Current to other motors, such as firing motor 802 or other driving motors, can also be controlled by electronics 810.

Electronics 810 is further coupled to receive instructions and provide data to system 800. System 800 can represent a combination of surgeon's console 52, electronics cart 56, processor 58, and display 60 of system 50 in FIG. 4. As such, system 800 includes one or more processors 802, memory 804, data storage 814, and a user interface 816. User interface 816 can be surgeon's console 52, display 60, keyboards, touchscreens, or other suitable input devices. Storage 814 can be any data storage system such as flash memory, a hard drive, CD reader or reader of other storage media, or other device for storing data. Memory 804 can include volatile and non-volatile memory for storage of data and processing steps. In some cases, memory 804 can be loaded with data, including programming steps, from storage 814.

In some embodiments, electronics 810 and electronics 806 may support integer math. Algorithms operating on electronics 806 and 810 can be scaled appropriately to perform mathematical operations assigned to them while controlling motors 804 and 802.

In operation, parameters regarding the operation of stapler 600 are read from memory 808 and provided to electronics 810 and processor 802. Surgeon input is received at user interface 816. Processor 802 executes instructions to translate the input to instructions for operation of stapler 600 and provides instructions to electronics 810. In some embodiments, the parameters read from memory 808 can be utilized in determining the instructions provided to electronics 810. Electronics 810 provides signals to the one or more motors 710 to provide the motions indicated by processor 802. Those motions are then translated to end effector 602. The signals provided to the one or more motors 710 may also be predicated on parameters read from memory 808. In some cases, processor 802 may provide or rewrite parameters in memory 808 to be utilized during the next utilization of stapler 600.

In general, motor assembly (or motor packs), staplers, and cartridges are not matched. During a procedure, any motor assembly can be utilized with any stapler and any of the various cartridges can be utilized in the stapler. Therefore, data storage 716 holds parameters associated with the stapler cartridge 614, memory 808 stores parameters associated with that particular stapler 600, and memory 812 stores parameters associated with that particular motor assembly 702.

Initialization of the Stapler

As discussed above, staple cartridges (also referred to as reloads) are available in a variety of sizes that are identified by color. Each color cartridge corresponds to a particular staple leg length. Common cartridges include green (4.3 mm leg length), blue (2.5 mm leg length), and white (1.5 mm leg length) cartridges 614. In order to properly form staples, anvil 610 and jaw 612 need to be positioned within close proximity to ensure that staples 652 hit pockets 654 in anvil 610 and form the desired "B" shape (FIG. 6B). Stapler 600 utilizes a "cantilever" style of clamping and, as discussed above, if the clamping torque limit is too high it is possible to deflect the tip of anvil 610 and jaws 612 away from each other to the point where staples 652 will not properly form when staples 652 are pushed out of cartridge 614 during the firing process. This situation may develop if there is too much tissue in the jaws during clamping with too much torque. To prevent this and ensure the proper tip gap is maintained, the clamping torque is limited.

Under ideal circumstances, if each of staplers 600 where identical, all staplers 600 would use the same torque limits. However, manufacturing variations and tolerances can result in significant variation between different staplers 600. According to the present invention, the torque limit can be customized for each of staplers 600. As a result, memory 808 can store the particular torque limit associated with that particular stapler 600. Furthermore, the torque limit can vary within an individual stapler 600 according to cartridge 614. Therefore, adjustments for type of cartridge 614 can also be stored in memory 808. In some embodiments, adjustments for type of cartridge 614 may not vary between staplers 600 and therefore a set cartridge variation can be provided by system 800 or stored in data storage 716 of each cartridge 614. During manufacturing, each stapler 600 is assembled and then operated to "wear-in" the clamping behavior.

Figure 9A:
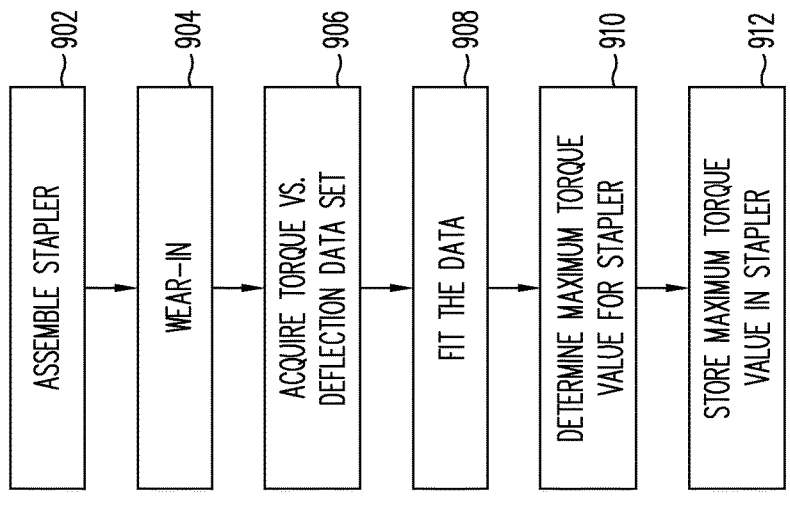
FIG. 9A illustrates a method of calibrating a surgical stapler according to some embodiments of the present invention.

In accordance with the present invention, a specific torque limit is determined for each stapler 600 and stored in memory 808 of chassis 608. FIG. 9A illustrates a procedure for initializing the torque limit for a particular stapler 600. In step 902, stapler 902 is assembled. After assembly, in step 904, stapler 600 is "worn-in" by repeatedly performing a clamping procedure. Stapler 600 is worn in when the torque required to clamp is relatively stable (i.e., does not change significantly between activations). In step 906, a series of shims of differing heights is utilized to enforce a known deflection of the tips of jaw 612 and anvil 610 during clamping. A data set of clamping torque as a function of tip deflection is then obtained.

Figure 9B:
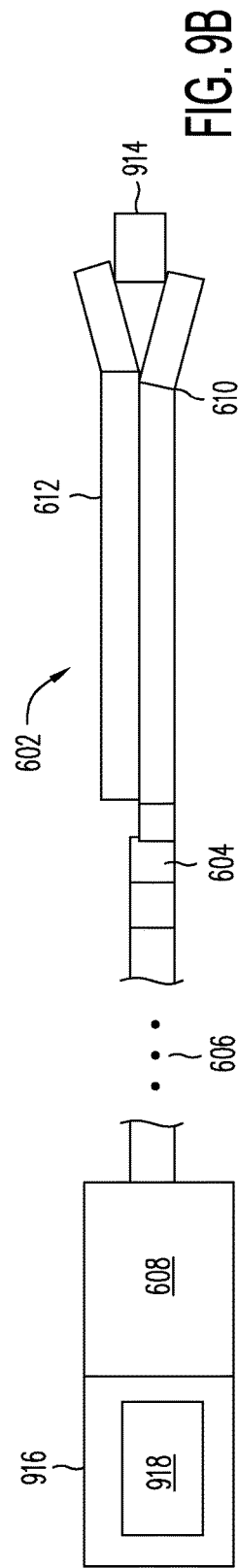
FIG. 9B illustrates a surgical stapler during calibration.
Figure 9C:
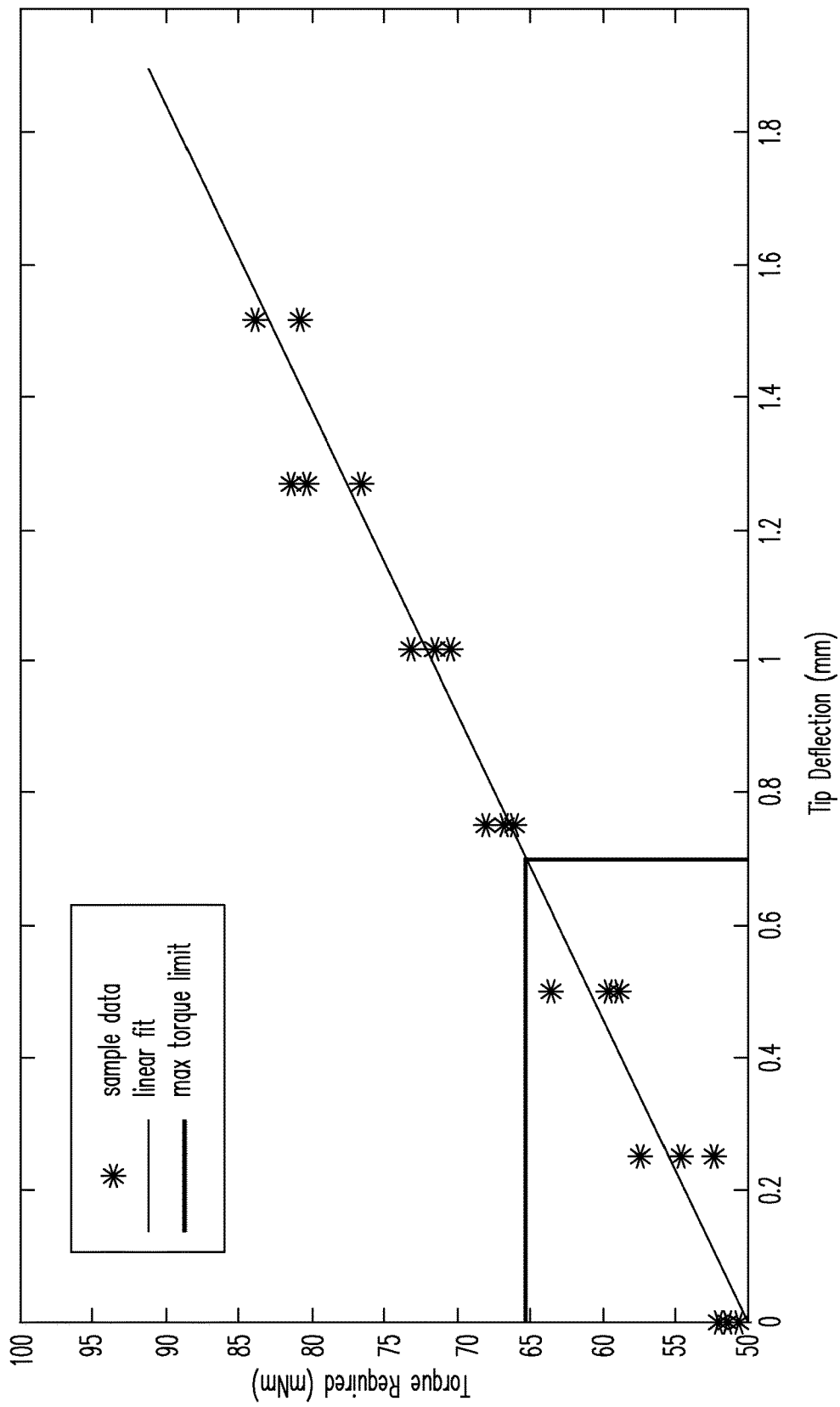
FIG. 9C shows example data obtained during a calibration procedure.

FIG. 9B illustrates deflecting the tips by a known amount with shim 914. As is shown in FIG. 9B, shim 914 enforces a particular tip separation while jaw 612 and anvil 610 are clamped. In step 906, a series of tests with different shims 914 are accomplished to produce the data set as shown in FIG. 9C. As shown in FIG. 9C, the X-axis represents the tip deflection enforced by each individual shim 914. The Y axis is the recorded torque data from a motor 918 in motor assembly 916 that drives chassis 608 of stapler 602 during the test to achieve a clamping condition. In some embodiments, a relationship between the feedback current of motor 918 and the torque applied by motor 918 and the resulting force between jaw 912 and anvil 610 is known based on previously acquired calibration data utilizing motor 918 and numerous instruments.

In step 908, the data can be fit to a function. In the example shown in FIG. 9C, the data is fit to a linear function Y=mx+b. A linear, least-squares method can be utilized to estimate the slope m and the offset b. In this linear equation, Y is the torque required and X is the tip deflection. As shown in FIG. 9C, torque is provided in milliNewton-meter (mNm) and deflection is provided in millimeters (mm). In the particular example provided in FIG. 9C, the slope m is determined to be 21.5 mNm/mm and the offset b is 50 mNm. As discussed above, the values for m and b vary due to manufacturing variance between different staplers.

In step 910 the maximum torque value is determined for stapler 600. In some embodiments, the maximum torque is determined by limiting the maximum tip deflection to 0.70 mm. The 0.70 mm is the tip separation that is appropriate for a blue cartridge 614, which can be considered to establish a safe baseline for a blue cartridge. This example value prevents improper formation of the staple during firing due to tip separation. As can be seen from FIG. 9C, or calculated by the above linear relationship, the particular stapler 600 illustrated in FIG. 9C has a maximum torque value of 65 mNm. Torque values above this may allow too much tip deflection (and therefore too large a tissue gap) for proper staple formation. By enforcing a torque limit, enough torque is supplied to the clamp, but too much torque is not allowed, which prevents larger tip deflections that result in improper staple formation.

In step 912, the maximum torque value for stapler 600 is stored in memory 808 of chassis 608 of stapler 600. The maximum torque value can then be read from memory 808 during operation of system 10, as illustrated in FIG. 8, and utilized to control the maximum torque supplied by motor 804 to end effector 602 during a stapling procedure.

In some embodiments, the calibrated maximum torque value, which can be designated as $\tau_{cal}$ is used as a baseline torque limit value for stapler 600. From this baseline, during operation, the actual torque can be adjusted for particular cartridges 614. The adjustment can be based on a large body of previously collected experimental and analytical data acquired utilizing multiple cartridges and multiple staplers that are loaded into system 800. As an example, adjustments for various cartridges 614 can be White=−3 mNm; Blue=+2 mNm; and Green=+9 mNm. These values are added to the maximum torque value and the adjusted value utilized to control the torque output of motor 804 of motor assembly 702. For example, if cartridge 614 was a blue cartridge, then the maximum torque value utilized during clamping is adjusted to 94 mNm.

The actual numbers utilized in the above description are for illustration only and should not be considering limiting. Each of stapler 600 may have a different maximum torque value. Additionally, in some embodiments different safe tip deflections or other parameters can be utilized. Further, adjustments for cartridge types may vary. Also, although the above discussion focused on a stapler instrument, similar calibrations can be performed on other instruments, for example vessel sealers.

Other parameters can also be set during calibration. For example, the calibrated torque limit can be set at a particular reference temperature $T_{ref}$. Other parameters may include wear coefficients, instrument life coefficients, and other parameters that relate to the particular stapler 600.

Adjusting and calibrating the maximum torque limit for each instrument allows more precise control of tip deflection during clamping. This can maximize instrument performance. By calibrating each instrument, a smaller margin can be utilized than if a single constant parameter was used uniformly across all instruments. Additionally, the uncertainty in the tip deflection during clamping can be reduced by more precisely controlling clamping. Further, manufacturing yields can be increased by reducing dependence on manufacturing tolerances and adjusting for manufacturing variations.

Initialization of Motors in the Motor Assembly

In addition to calibrating and initializing stapler 600, motor assembly 702 can also be calibrated and initialized to adjust for manufacturing variations. Manufacturing variances in clamping motor 804 and firing motor 802 as well as in mechanical converter 714 lead to variations between motor assemblies. During motor assembly calibration, motor speed vs no-load current relationships $I_{NL}$ and the torque constant $K_T$ for each of clamping motor 804 and firing motor 802 are determined.

FIG. 10A illustrates a calibration method 1000 that can be utilized to calibrate each of motors 804 and 802 of motor assembly 702. As shown in method 1000, step 1002 is to acquire an assembled motor assembly 702. In step 1004, an initial calibration is performed. An example of a calibration procedure is illustrated in FIG. 10B. In step 1006, motors 802 and 804 of motor assembly 702 are worn in. During the wear-in process, each of motors 802 and 804 are driven many cycles against a constant torque in order to break in the geartrain of mechanical converter 714 and ensure that the grease is evenly distributed. In step 1008, a final calibration is performed. The final calibration of step 1008 and the initial calibration of step 1004 can be the same calibration method, an example of which is shown in FIG. 10B. In step 1010, the calibrated parameters are stored in memory 812 of motor assembly 702.

Figure 10C:
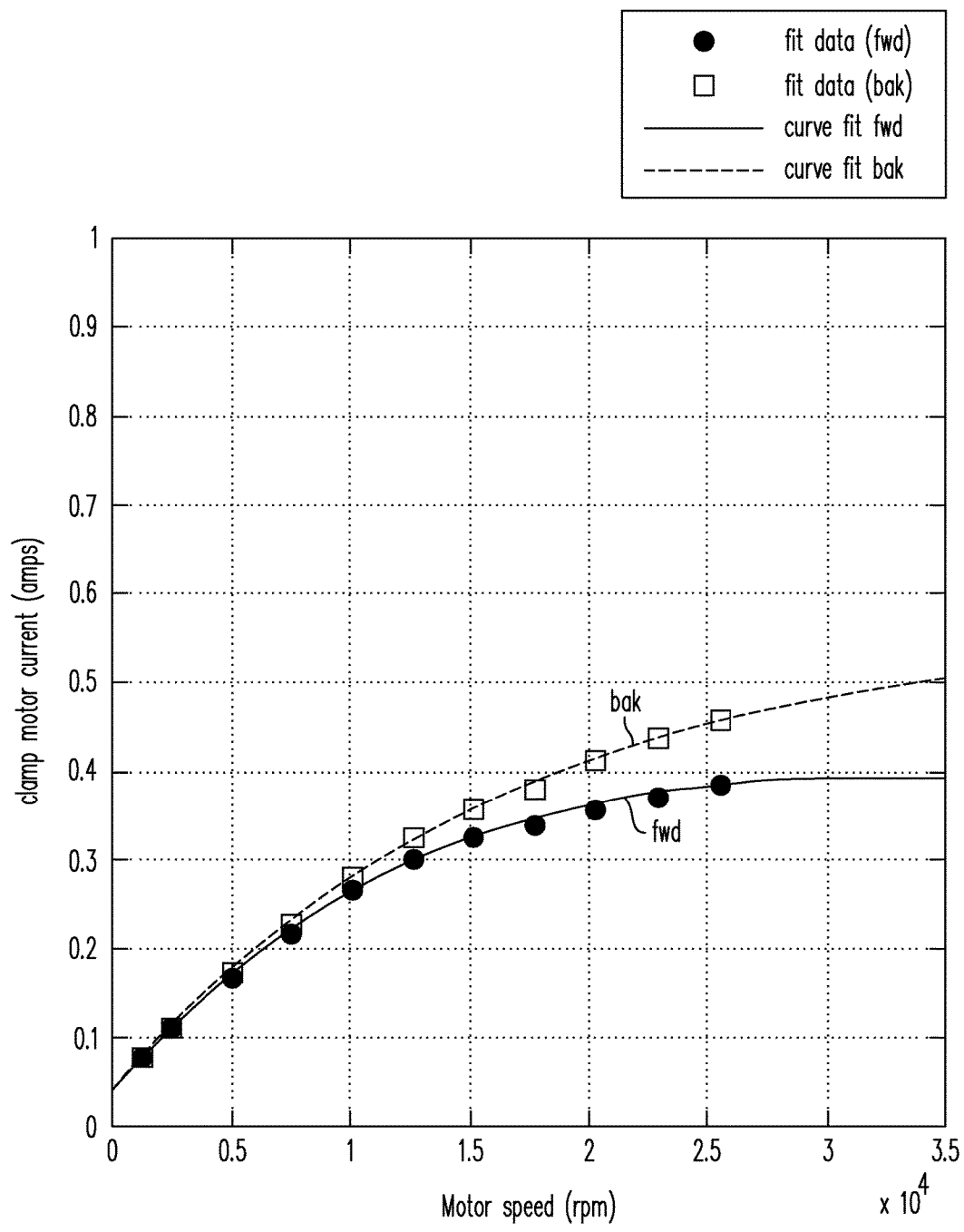
FIGS. 10C and 10D illustrate calibration of a no-load current for motors in a motor assembly according to some embodiments of the present invention.

FIG. 10B illustrates an example of a calibration procedure 1012 that can be utilized in steps 1004 and 1008 of FIG. 10A. As shown in FIG. 10B, step 1014 is to acquire no-load data for the motor, which could be either clamping motor 804 or firing motor 802. To determine the relationship between motor speed and no-load current for a motor, the motor is driven at various speeds, one at a time in the forward direction first then in the backward direction. No-load current draw data is measured, as well as the temperature of motor assembly 702 while achieving each of the various speeds. In some cases, the no load current draw can be adjusted for temperature. As an example, the speed progression in $10^4$ rotations per minute (rpm) may be [2.5, 1.5, 2.25, 0.5, 2.0, 0.75, 1.0, 1.75, 0.25, 1.25, and 0.125]. However, other data taking progressions can be utilized. FIG. 10C illustrates data for a clamp motor 804 current as a function of motor speed in the forward (fwd) and backward (bak) directions.

In step 1016 the data is fit to a function, for example an exponential function or a linear function, to determine a relationship between motor current and motor speed. For example, a linear function with non-polynomial terms that can be used to fit the data can be given by:

$$y = c1 + c2 * e^{-x * xscale} + c3 * x * e^{-x * xscale}$$

where c1, c2, c3 are coefficients and x_scale is a constant.

In FIG. 10C, the solid curves represent a curve fit to the data. The data may be adjusted for temperature and filtered prior to fitting. In some embodiments, the raw data can be adjusted as a function of temperature based on previous modeling of motors as a function of temperature. Additionally, the raw data can be filtered as a function of time to reduce noise and provide averaging.

Figure 10D:
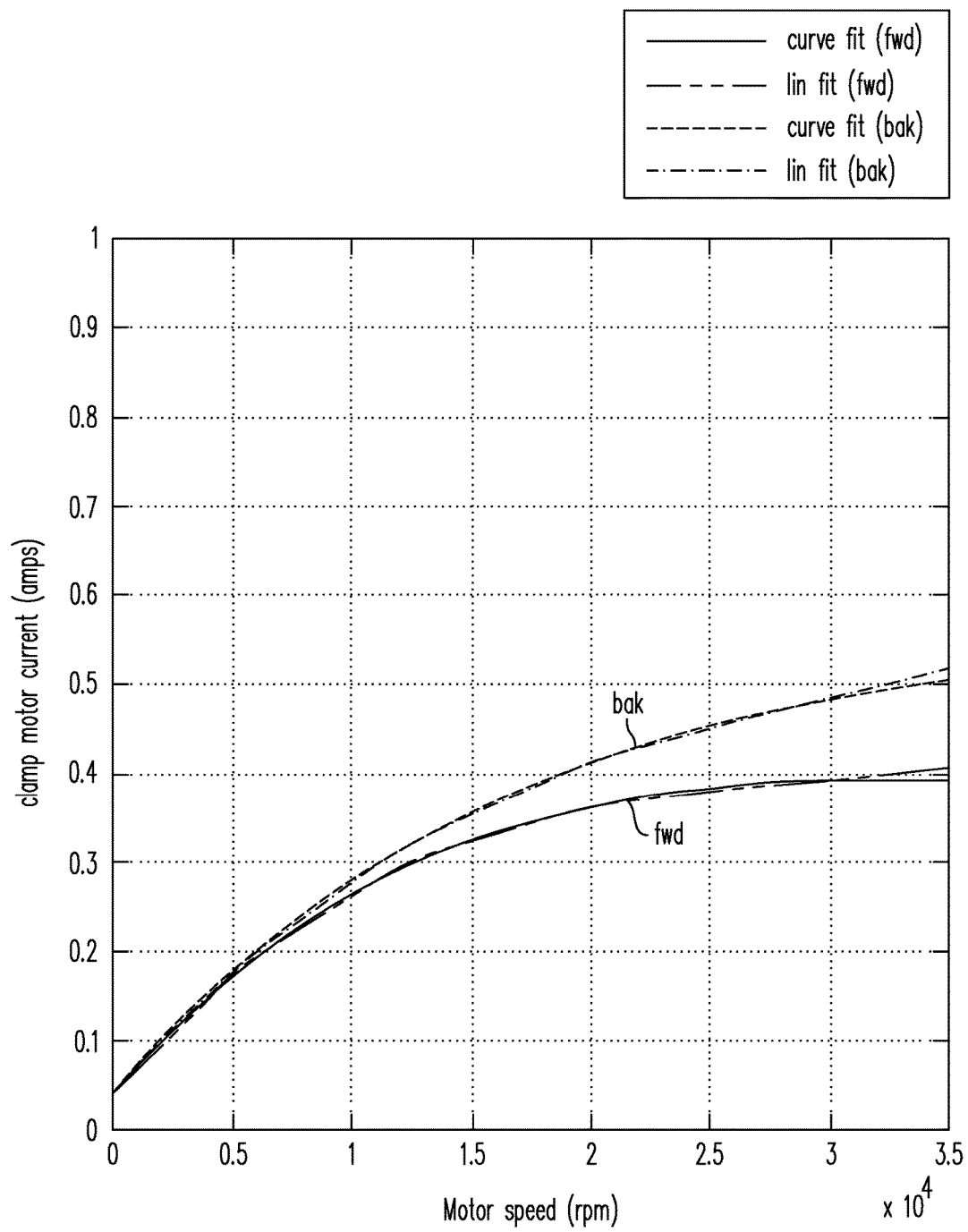

In some embodiments, a linear piecewise approximation can be optimized to fit the function in order to ease further computation. A linear piecewise approximation to the curve fit functions shown in FIG. 10C is illustrated in FIG. 10D. The linear piecewise approximation can eventually be stored in memory 812 as $I_{NL}$.

Once the no-load current calibration is completed, procedure 1012 proceeds to determination of a torque constant $K_T$ (the torque output per current input). As shown in FIG. 10B, step 1018 includes acquiring torque loading data. In acquiring the torque loading data, the motor being calibrated (clamping motor 804 or firing motor 802) is driven first against no load and then the load is ramped up to a known torque loading and then ramped back down to no-load. The known torque loading can be provided by an external source such as a brake or dynamometer, for example. Data (i.e. torque output vs. current load) is gathered in both the forward and backward directions for the motor being calibrated. Multiple sets of data can be taken for each of clamping motor 804 and firing motor 802.

In step 1020, the torque data is analyzed to determine the torque constant $K_T$. The data can be filtered and the torque constant $K_T$ determined by comparing the change in torque (no load to known torque loading) to the change in current (current at no load to the current at the torque loading). Calculations for the multiple sets of data taken during step 1018 can be averaged to determine the final calibration torque constant value.

Figure 10E:
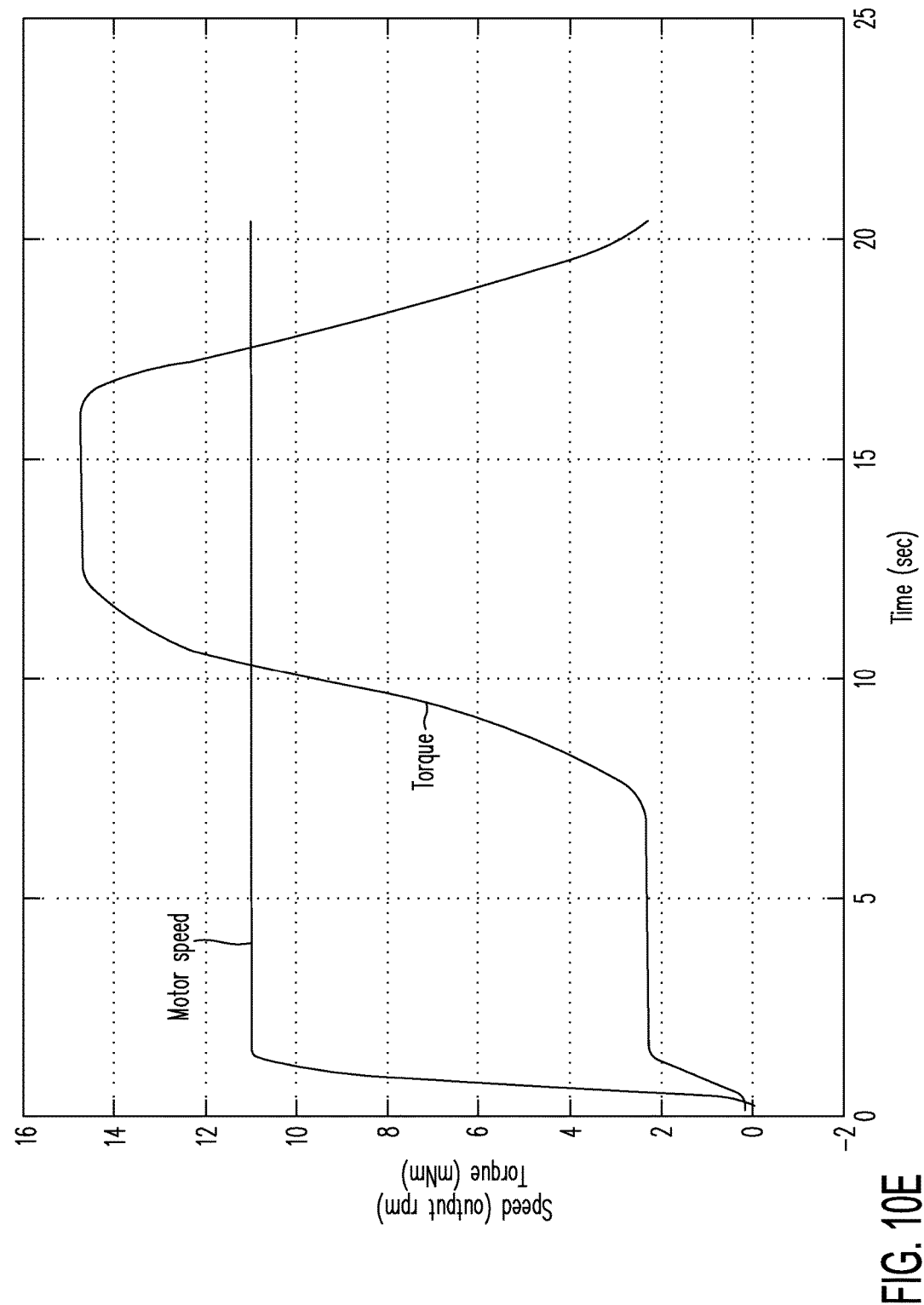
FIGS. 10E and 10F illustrate calibration of a torque constant for motors in a motor assembly according to some embodiments of the present invention.
Figure 10F:
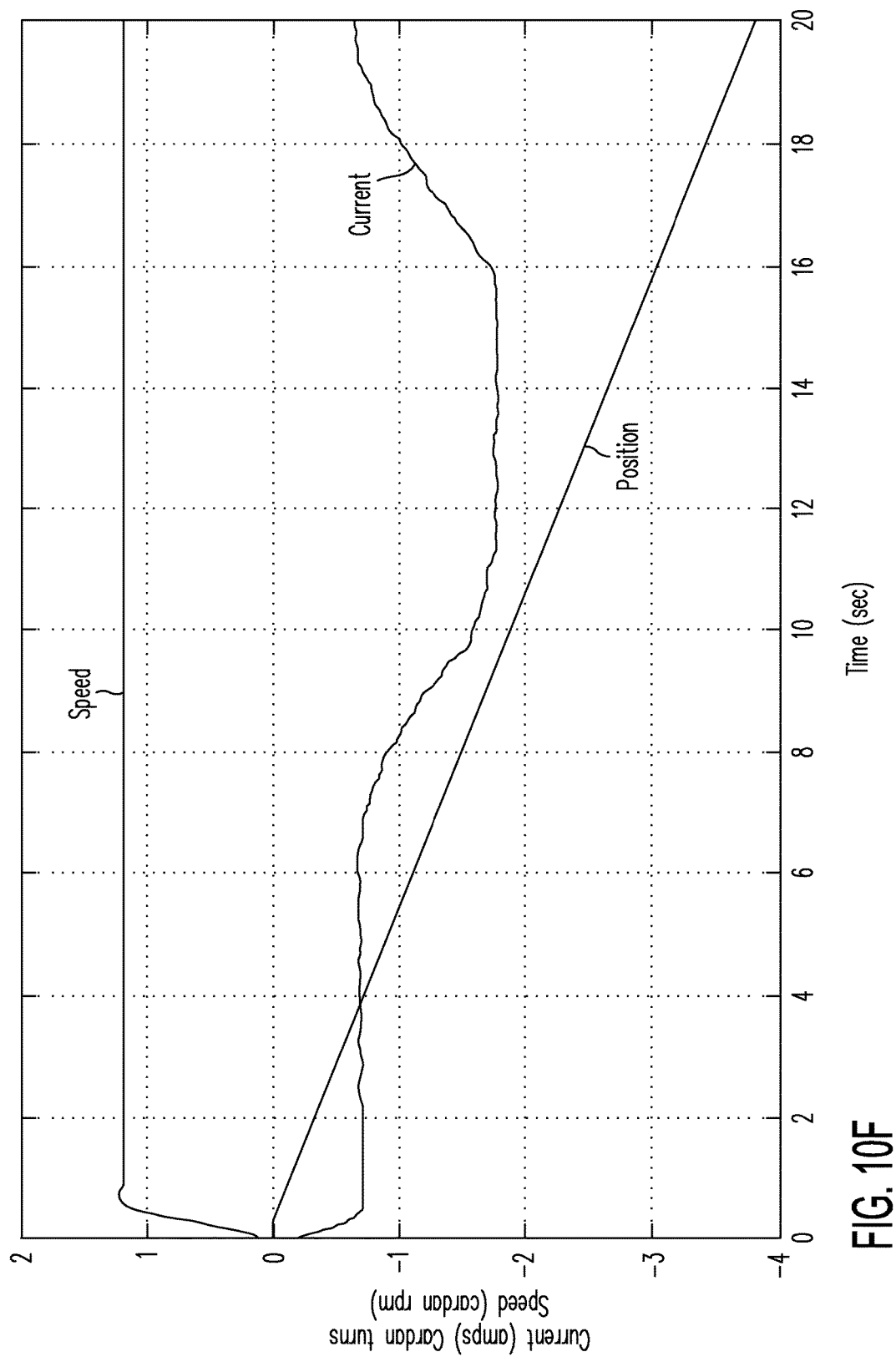

FIG. 10E illustrates an example of motor speed and torque versus time for a motor during data acquisition step 1018 according to some embodiments of the present invention. FIG. 10F illustrates motor speed, current, and cardan position as a function of time corresponding to the data shown in FIG. 10E. As shown in FIG. 10F, the current data can be filtered to obtain a continuous function of current versus time for the test.

As illustrated in FIG. 10A, in step 1010 after the final calibration step 1008 both the no-load current calibration data $I_{NL}$ and the torque loading calibration data $K_T$ can be stored in memory 812 of motor assembly 702 and can be utilized during further calculations of torque limits for motor assembly 702 as discussed further below.

Torque Limit Compensation

Referring back to FIG. 8, stapler 600 is only allowed to fire when stapler 600 reaches a full clamp condition. The amount of torque provided by motor 804 to reach a complete clamp condition is limited by software. This torque limit is generally set as a current limit, which is a limit on the current that motor 804 is allowed to draw during the clamping process. The current limit is a function of the calibration data for the stapler 600, as discussed above. In other words, initially the torque limit is set at $\tau_{cal}$ as indicated above, adjusted according to the color of cartridge 614.

However, with repeated use of stapler 600, the effective torque limit can drift and deviate from the original calibration data. In other words, the same torque that it takes to clamp stapler 600 after several uses is different from, and typically less than, the torque that it took to clamp stapler 600 at its initial calibration state. If the torque limit were left unchanged, stapler 600 might be allowed to reach a complete clamp actuation on challenge materials that it was not intended for, causing unintentional increased deflection of the tips between jaws 612 and anvil 610. The increased tip deflection, as discussed above, provides for an inadequate tissue gap and improperly formed staples if the stapler were fired.

In accordance with some embodiments of the present invention, the torque limit utilized for stapler 600 is adjusted according to multiple operating parameters. The multiple operating parameters can, for example, include the temperature of motor assembly 702, the articulation angle of wrist 604, the lifetime use of motor assembly 702 (e.g. the number of stapler firings affected by motor assembly 702), and the lifetime use of stapler 600 (e.g. the number of stapler firings using stapler 600). The actual torque limit can be adjusted during operation in order to adjust for the age and operating condition of stapler 600.

Figure 11:
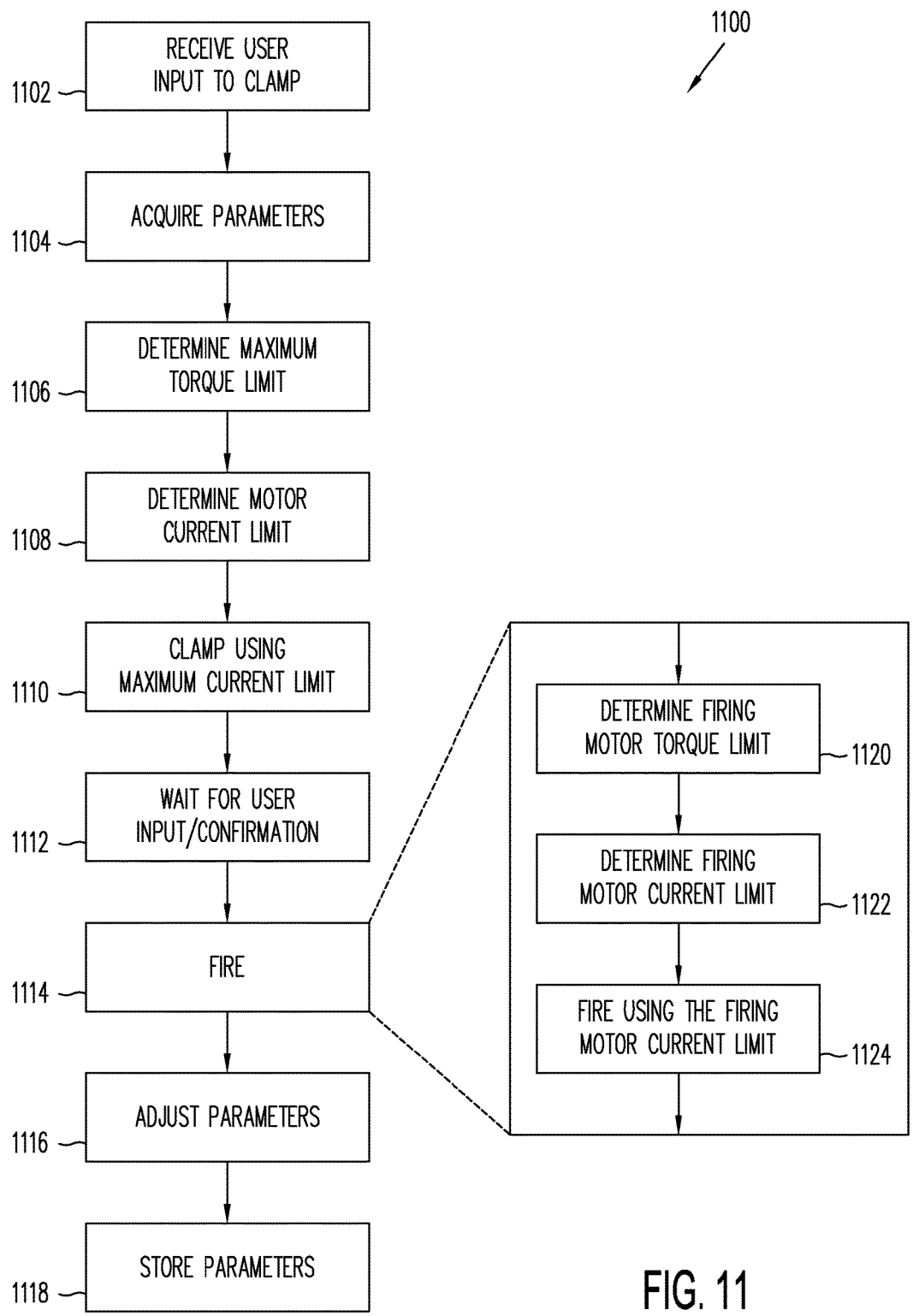
FIG. 11 shows a method of adjusting torque limits for a surgical stapler during operation.

FIG. 11 illustrates an algorithm 1100 for performing such an operation. Algorithm 1100 can be performed by system 800 or system 800 in combination with processor 810 in motor assembly 702. As shown in step 1002, algorithm 1100 is started when a command is received to clamp, prior to firing, stapler 600 in step 1102.

In step 1104, the parameters that are specific to stapler 600, which are stored in memory 808 of chassis 608, the parameters that are specific to motor assembly 702, which are stored in memory 812 of motor assembly 702, and the parameters that are specific to cartridge 614, which are stored in data storage 716, are retrieved. In step 1106, the adjusted maximum torque limit is determined. The adjusted maximum torque limit can be determined based on a number of parameters and a model that fits the wear characteristics of motor assembly 702 and stapler 600 in combination with a particular cartridge 614. As discussed above, some of the factors that can be including in the model include the temperature of motor assembly 702 (T), the lifetime of motor assembly 702 measured by the number of stapler firings ($L_{MP}$), the lifetime of stapler 600 measured by the number of stapler firings ($L_{Inst}$), and the angle of wrist 604 ($\theta$). In general, a set of parameters {Parameters} can be defined that affect the torque limit utilized. In some embodiments, the set can be defined as $\{T, L_{MP}, L_{Inst}, \theta, \ldots\}$ Other parameters may also be utilized in the model.

Therefore, the adjusted maximum torque limit can be given by $$\tau_{com} = F(\{Parameters\})$$

where the function F defines the model that best fits the behavior of clamp 600 and motor assembly 702 over their lifetimes. The function F can be determined empirically over a large set of staplers 600 and motor assemblies 702 to accurately represent the wear characteristics over time. In some cases, factors related to the various parameters may be scalars in the model while in other cases a better model has certain factors being additive while other factors are scalars. For example, a model for calculating the maximum torque limit may be given by $$\tau_{com}=F(\{Parameters\})=f(T)*g(L_{MP})*h(L_{inst})*y(\theta)+z(T)+k(L_{MP})+x(L_{inst})+p(\theta)+C,$$

where f, g, h, y, z, k, x, and p represent particular functions of the indicated parameters and C represents a general offset term. As shown in the above equation, the corrections can include scalar components and additive components for each of the parameters in the parameter set. In some models, certain of functions f, g, h, and y can be set to one (1) if that parameter is not a scalar component while functions z, k, x, and p are set to 0 if the corresponding parameter is not an additive component. The above example of F{Parameters} is not limiting and other functions can be utilized in the modeling. Some particular example models are presented in further detail below.

In step 1108, the motor current limit is determined from the torque limit. As an approximation, there is a linear relationship between the current and the desired torque for motor 804. Therefore, conversion from torque limit to current limit involves scaling the torque limit according to the linear relationship to determine the current limit for motor 804 in the clamping process.

In step 1110, stapler 600 is clamped utilizing the adjusted motor current limit described above. As discussed above, stapler 600 is clamped when motor 804 achieves a particular position while not exceeding the adjusted motor current limit. Once stapler 600 is in a clamped condition, then stapler 600 can be fired. In step 1112, after a successful clamping is achieved, algorithm 1100 waits for a user input or confirmation prior to firing. In step 1114, stapler 600 is fired.

As shown in FIG. 11, in some embodiments firing step 1114 can include determining the firing torque limit 1120, determining the firing motor current limit 1122, and firing using the firing motor current limit 1124. Excessive torque applied to a fire cardan joint in stapler 600 can pose a problem to breaking the fire cardan joint or breaking the leadscrew in cartridge 614. Excessive torque could also cause knife 616 in cartridge 614 to be jammed against a hard stop with too much force, possibly breaking a piece of knife 616 into the patient. Both the drive train and cartridge leadscrew and knife mechanisms should include an adequate safety margin to prevent breakage during operation. The firing torque limit (the torque limit of firing motor 802) can be adjusted to prevent the torque being applied to the mechanism to approach a level that damages stapler cartridge 614 or cartridge drivetrain components.

Determining the firing torque limit for firing motor 802 in step 1120 can be similar to determining the torque limit for clamping motor 804 as discussed above with respect to step 1106. As discussed above, the firing torque limit for firing motor 802 can be adjusted using a function of, for example, temperature, motor assembly life, instrument life, and other parameters. The same forms of the adjustment equations, in some cases with different coefficients, can be used in adjusting the torque limit for firing motor 802 as those discussed above can be used for adjusting the torque limit for clamping motor 804. Further, the same form of equation for determining the motor current limit as discussed above with step 1108 can be utilized in step 1122. Firing step 1124 is complete when firing motor 802 reaches a particular position while not exceeding the firing motor current limit.

In step 1116, parameters are adjusted to reflect the firing. For example the parameters $L_{MP}$ and $L_{inst}$ can both be incremented. In step 1118, the adjusted parameters can be stored for future use. For example, $L_{MP}$ is stored in memory 812 and $L_{inst}$ is stored in memory 808 for use in the next stapling procedure involving motor assembly 702 or stapler 600.

As discussed above, the torque limit can be translated to a current limit for motor 804 in step 1108. In some cases, the relationship between the current limit and the torque limit can be given by:

$$I_{limit} = I_{NL} + \frac{\tau_{com}}{K_T},$$

where $I_{limit}$ is the current limit provided to motor 804, $I_{NL}$ is the no-load current for motor 804 at the time of calibration, $K_T$ is a torque constant characteristic of the motor assembly drive train, and $\tau_{com}$, as discussed above, represents a modeled and compensated torque limit provided to minimize error in clamping. $I_{NL}$ represents the friction compensation for the motor assembly and can be a function of speed. The parameter $K_T$ is related to the conversion of torque to current in motor 804. Initial $K_T$ at a reference temperature $T_{ref}$ may be determined during a calibration of motor assembly 702 as discussed above. In some models, $K_T$ can be given by $$K_T=K_{Tcal}*[1-\eta*(T-T_{ref})],$$

where $K_{Tcal}$ is the calibrated conversion coefficient and $\eta$ is a temperature coefficient related to the operation of motor 804. In some models, the value for $I_{NL}$ can be given by:

$$I_{NL}=I_{cal}*[1-\mu*(T-T_{ref})]*[1-\kappa*(L_{MP})],$$

where $I_{cal}$ is the calibrated no-load current draw representing the loss in the motor assembly 702 as a function of speed, $\mu$ is the temperature coefficient, T is the temperature of motor assembly 702 (measured by electronics 810), $T_{ref}$ is a reference temperature, $\kappa$ is the motor assembly life coefficient, and $L_{MP}$ is the number of times that motor assembly 702 has fired a stapler. The reference temperature $T_{ref}$ can, for example, be the temperature at which motor assembly 702 is calibrated and can be stored in memory 812. As can be seen from the above equations in this model, the calibrated current limit for stapler 600 at $T=T_{ref}$ is given by $I_{limit}=I_{cal}+\tau_{cal}/K_{Tcal}$, which can be used in the initial calibration phase to determine both $I_{cal}$ and $K_{Tcal}$. The values of $I_{cal}$ and $K_{Tcal}$ can, in some embodiments, be stored in memory 812.

In some models, the adjusted torque limit can be given by $$\tau_{com}=\tau_{des}*W(\theta)*[1-\alpha*(T-T_{ref})]*[1-\beta*(L_{MP})]*[1-\gamma*(L_{ins})]+\delta*(T-T_{ref})+\epsilon$$

where $\alpha$ is a temperature coefficient, $\beta$ is the life coefficient of motor assembly 702, $\gamma$ is the life coefficient of stapler 600, $\delta$ is the constant offset temperature coefficient and $\epsilon$ is a constant offset. The value of $\tau_{des}$ can be given by the sum of $\tau_{cal}$ and cartridge adjustment, as discussed above.

The function W reflects the added friction when wrist 604 is articulated. In some embodiments, the function W is a cosine function of the angle $\theta$ through which wrist 604 is articulated. As such, in some embodiments W can be given by $$W(\theta) = \frac{1}{1-\xi(1-\cos(\theta))}$$

where θ is the wrist angle of wrist 604 as shown in FIG. 8 and ξ is the parameter that determines the influence of the wrist angle on the torque limit. As illustrated, at θ=0 degrees, W(θ) will be 1. As the angle increases, however, the friction at wrist 604 increases, resulting in a multiplicative increase in $\tau_{com}$ by W(θ). In some embodiments, the function W(θ) can be implemented as a look-up table. The torque limit wrist adjustment W(θ) can be utilized for any surgical instrument with a wrist and the need to transmit a force through the wrist.

The various scalar coefficients shown above can be adjusted to best model the lifetime behavior of motor assembly 702 and of stapler 600. These coefficients include the temperature coefficients η, μ, α, and δ; the lifetime coefficients κ, β and γ; additive coefficient ε; and wrist coefficient ξ and can be determined through repeated testing of various ones of stapler 600 and motor assembly 702 through their lifetimes or in some cases can be customized through calibrations done on individual motor assemblies or instruments. In some embodiments, if the coefficients are determined by averaging over a large number of motor assemblies and staplers and do not vary between individual motor assemblies or staplers, then they can be stored in system 800 where the modeling is calculated. Otherwise, the coefficients can be stored with their individual components. For example, the temperature coefficients η, μ, α, and δ; the lifetime coefficients κ and β can be stored in memory 812 while the lifetime coefficient γ can be stored in memory 808.

As indicated above, for example δ can be set to 0 if temperature is a scalar component not an additive component and α can be set to 0 if temperature is an additive component and not a scalar component. In this model, with α and δ both non zero temperature is both a scalar and additive factor. In some embodiments, the coefficients can be within the following ranges: $0 \le \alpha \le 1$; $0 \le \beta \le 1$; $0 \le \delta \le 1$; $-10 \le \epsilon \le 10$; $0 \le \gamma \le 1$; $0 \le \mu \le 1$; $0 \le \kappa \le 1$; $0 \le \eta \le 1$; and $0 \le \xi \le 1$. In many cases, the coefficients are less than about $10^{-2}$.

The primarily scalar model example provided above is not the only model that can be utilized to adjust the torque limits for operation of stapler 600 for lifetime drift as a function of temperature. Other models may utilize, for example, a primarily additive model or combinations of additive and scalar components can be added, or nonlinear models could be used. Models can be expanded as needed to include combinations of multiplicative and additive factors in order to best model the behavior of stapler 600 during its lifetime of use.

As suggested above, there is a variety of models that can be utilized to model the adjustment to the torque limits. As suggested above, depending on the system, certain variables may be modeled as an additive effect and others may be modeled as a multiplicative effect. In some embodiments, the model can be tailored for the lifetime of a particular stapler system. This can be accomplished by setting some of the parameters to zero and some to non-zero values. In some embodiments, the modeling equation for $\tau_{com}$ can be expanded to include more additive factors and further combinations of additive and multiplicative factors in the modeling.

The current limit utilized to control clamp motor 804, $I_{limit}$, can be provided to electronics 810 in order to control motor 804. The model utilized to provide the adjusted current limit operates to provide proper clamping throughout the operable lifetimes of stapler 600 and of motor assembly 702. The torque compensation algorithm described above allows the surgical system utilizing stapler 600 to effectively and safely clamp on appropriate materials (and thicknesses) while maintaining appropriate tissue gap and may prevent a full clamp on materials (and thicknesses) that would cause inadequate tissue gap. This operation helps to prevent excessive tip deflection and also prevents firing and causing improperly formed staples and surgical intervention that would result from improperly formed staples.

Homing Adjustments

In some embodiments of the invention, a homing procedure can be provided to further adjust the torque limits. The homing procedure is implemented when stapler 600 and motor assembly 702 is first attached to patient side cart 22. In some embodiments, system 800 can drive stapler 600 through a preset range of motions and tests while monitoring the corresponding performance of stapler 600 and motor assembly 702. Current, position, and torque of motors 804 and 802 can be monitored by electronics 810 and communicated to processor 800. Processor 800 can adjust coefficients and parameters to correct for the measured behavior of stapler 600 and motor assembly 702 during homing. Those corrected coefficients and parameters can be utilized while operating stapler 600 with motor assembly 702 as described above.

Individual parameters can be adjusted according to the performance tests. As such, the calibration data, for example $\tau_{cal}$, can be adjusted as a result of the homing process in addition to the factors described above prior to utilization of stapler 600.

The above detailed description is provided to illustrate specific embodiments of the present invention and is not intended to be limiting. Numerous variations and modifications within the scope of the present invention are possible. The present invention is set forth in the following claims.

What is claimed is:

1. A method of calibrating a motor in a motor assembly, comprising:
   acquiring an assembled motor assembly, the motor assembly including the motor, a memory to store predetermined calibrated parameters of the motor, and electronics coupled to the memory and the motor, the electronics including interfaces to couple with a clamping device and a system, external to the motor assembly, to control operation of the motor, the electronics being configured to:
   retrieve the predetermined calibrated parameters from the memory;
   provide the predetermined calibrated parameters to the external system; and
   receive control signals for driving the motor from the external system, the control signals being based on the predetermined calibrated parameters;
   performing a final calibration of the motor; and
   storing calibration data in the memory of the motor assembly;
   wherein the predetermined calibrated parameters comprise a motor speed versus no load current relationship for the motor determined by a procedure including:
   acquiring no-load data for the motor; and
   fitting a function to the no-load data to determine the motor speed versus no load current relationship.

2. The method of claim 1, wherein the calibration data includes a motor speed versus no-load current relationship $I_{NL}$ and a torque constant $K_T$.

3. The method of claim 2, wherein performing the final calibration includes
   acquiring no-load data for the motor;
   fitting a function to the no-load data to determine $I_{NL}$;
   acquiring torque loading data for the motor; and determining the torque constant $K_T$ from the torque loading data.

4. The method of claim 3, wherein $I_{NL}$ is a function of motor speed and direction.

5. The method of claim 3, further including fitting a linear piecewise function to approximate the function.

6. The method of claim 1, further including wearing in the motor prior to performing the final calibration.

7. The method of claim 1, further including performing an initial calibration of the motor prior to wearing in the motor.

8. The method of claim 1, further including storing lifetime data in the memory of the motor assembly.

9. The method of claim 5, wherein the lifetime data includes a motor assembly lifetime.

10. The method of claim 1, wherein the motor is a clamping motor.

11. The method of claim 1, wherein the motor is a firing motor.

12. A motor assembly, comprising:
at least one motor;
a memory to store predetermined calibrated parameters of the at least one motor; and
electronics coupled to the memory and the at least one motor, the electronics including interfaces to couple with a clamping device and a system, external to the motor assembly, to control operation of the at least one motor, the electronics being configured to:
retrieve the predetermined calibrated parameters from the memory;
provide the predetermined calibrated parameters to the external system; and
receive control signals for driving the motor from the external system, the control signals being based on the predetermined calibrated parameters;
wherein the predetermined calibrated parameters comprise a motor speed versus no load current relationship for the at least one motor determined by a procedure including:
acquiring no-load data for the at least one motor; and
fitting a function to the no-load data to determine the motor speed versus no load current relationship.

13. The motor assembly of claim 12, further including wearing in the at least one motor prior to performing a final calibration.

14. The motor assembly of claim 13, further including performing an initial calibration of the at least one motor prior to wearing in the at least one motor.

15. The motor assembly of claim 14, wherein the performing the procedure further includes:
acquiring torque loading data for the at least one motor; and
determining a torque constant $K_T$ from the torque loading data.

16. The motor assembly of claim 14, wherein the memory also stores lifetime data.

17. The motor assembly of claim 16, wherein the lifetime data includes a motor assembly lifetime.

18. The motor assembly of claim 14, wherein the at least one motor includes a clamping motor.

19. The motor assembly of claim 14, wherein the at least one motor includes a firing motor.

* * * * *